(12) United States Patent
Ide

(10) Patent No.: US 11,452,645 B2
(45) Date of Patent: Sep. 27, 2022

(54) ABSORBENT ARTICLE

(71) Applicant: Daio Paper Corporation, Ehime (JP)

(72) Inventor: Aya Ide, Ehime (JP)

(73) Assignee: Daio Paper Corporation, Ehime (JP)

( * ) Notice: Subject to any disclaimer, the term of this patent is extended or adjusted under 35 U.S.C. 154(b) by 467 days.

(21) Appl. No.: 16/491,252

(22) PCT Filed: Mar. 6, 2018

(86) PCT No.: PCT/JP2018/008470
§ 371 (c)(1),
(2) Date: Sep. 5, 2019

(87) PCT Pub. No.: WO2018/168561
PCT Pub. Date: Sep. 20, 2018

(65) Prior Publication Data
US 2020/0030160 A1 Jan. 30, 2020

(30) Foreign Application Priority Data
Mar. 17, 2017 (JP) .............................. JP2017-052394

(51) Int. Cl.
*A61F 13/511* (2006.01)
*A61F 13/475* (2006.01)
(Continued)

(52) U.S. Cl.
CPC .......... *A61F 13/511* (2013.01); *A61F 13/475* (2013.01); *A61F 13/494* (2013.01); *A61F 13/496* (2013.01)

(58) Field of Classification Search
CPC ................. A61F 13/475; A61F 13/494; A61F 13/49413; A61F 13/4942; A61F 13/49446;
(Continued)

(56) References Cited

U.S. PATENT DOCUMENTS 5,167,653 A * 12/1992 Igaue ................... A61F 13/4942
604/385.04
5,490,847 A * 2/1996 Correa ................... A61F 13/476
604/385.04
(Continued)

FOREIGN PATENT DOCUMENTS

JP S63-235501 9/1988
JP 2001-046430 2/2001
(Continued)

OTHER PUBLICATIONS

International Search Report for PCT/JP2018/008470, dated Jun. 5, 2018.

*Primary Examiner* — Michele M Kidwell
(74) *Attorney, Agent, or Firm* — Andrus Intellectual Property Law, LLP

(57) ABSTRACT

A flow of an excretion liquid into a side pocket is accomplished with a simple structure using an imperforated sheet. A side pocket extending in a front-back direction LD is disposed in an absorbent article on a lateral side of an absorber. The side pocket is surrounded by a side cover portion reaching the back surface side of the absorber from above a side of a top sheet via an upper portion, an outer side, and a lower portion of the side pocket. A portion located above the side of the top sheet in the side cover portion includes a non-bonded portion not bonded to the top sheet and a bonded portion located on both front and back sides of the non-bonded portion. A gap between the side cover portion and the top sheet in the non-bonded portion is open above the top sheet and toward the side pocket.

6 Claims, 16 Drawing Sheets

(51) Int. Cl.
*A61F 13/494* (2006.01)
*A61F 13/496* (2006.01)

(58) Field of Classification Search
CPC .................. A61F 13/496; A61F 13/511; A61F 2013/4944; A61F 5/451
See application file for complete search history.

(56) References Cited

U.S. PATENT DOCUMENTS

| | | | | |
|---|---|---|---|---|
| 5,921,975 | A * | 7/1999 | Suzuki | A61F 13/4753 604/385.04 |
| 2014/0316365 | A1 * | 10/2014 | Tsang | A61F 13/49 493/393 |
| 2016/0113823 | A1 * | 4/2016 | Iwasaki | A61F 13/4758 604/385.26 |

FOREIGN PATENT DOCUMENTS

| | | |
|---|---|---|
| JP | 2002-102282 | 4/2002 |
| JP | 2009-082358 | 4/2009 |
| JP | 2009-118896 | 6/2009 |
| JP | 2012-095790 | 5/2012 |
| JP | 2013-255849 | 12/2013 |
| JP | 2015-104543 | 6/2015 |
| JP | 2016-112208 | 6/2016 |
| JP | 2016-189819 | 11/2016 |

* cited by examiner

FIG.3 (a)
FIG.3 (b)
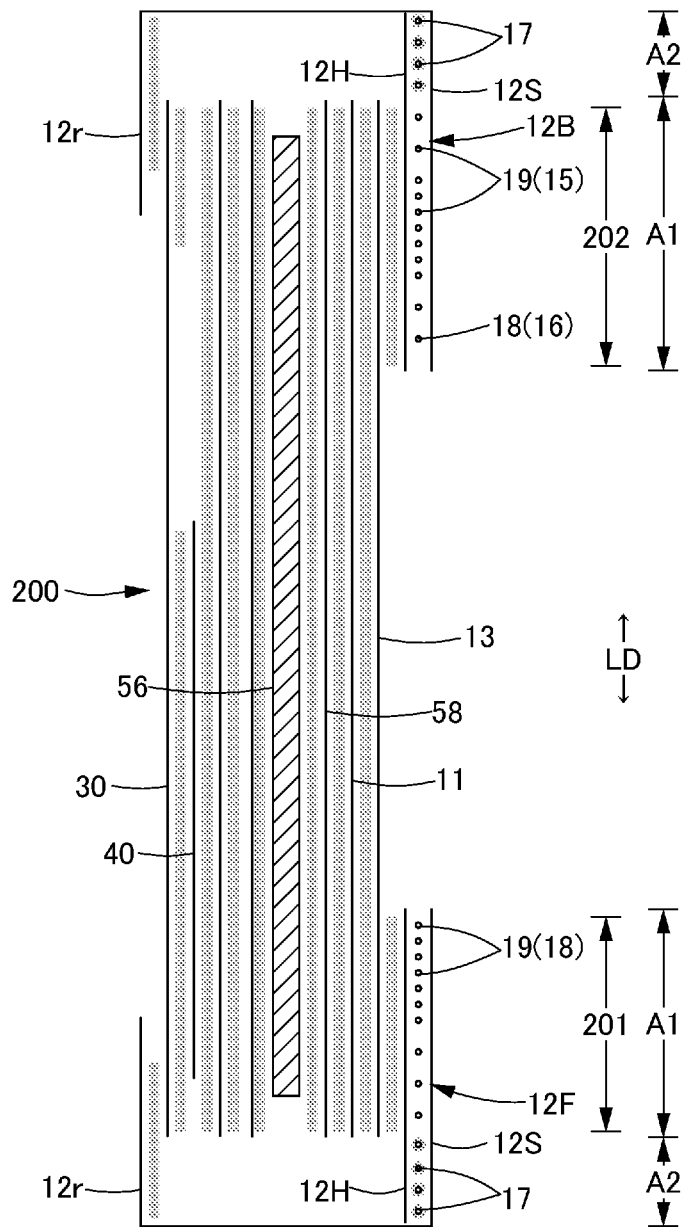
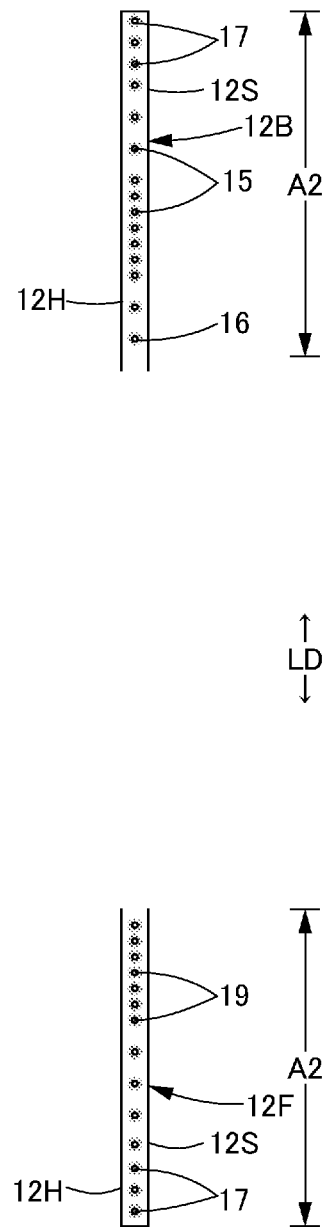

FIG.16 (a)
FIG.16 (b)
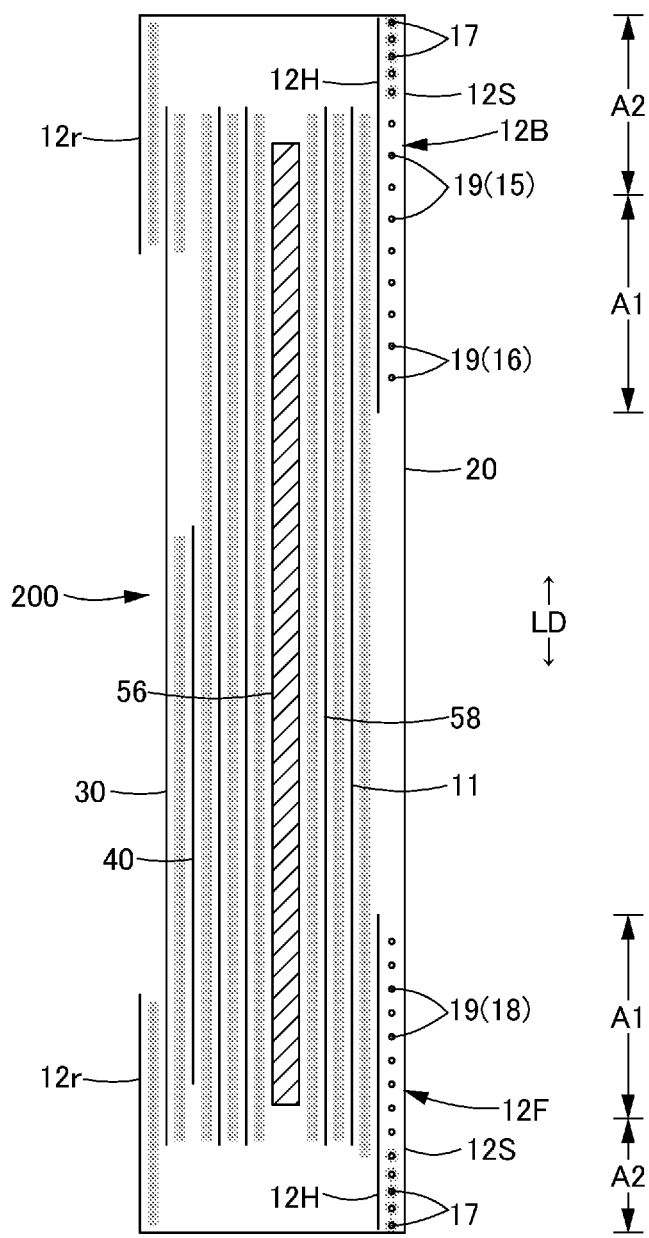
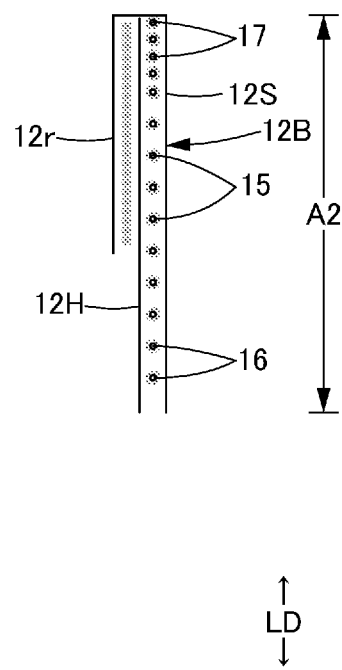
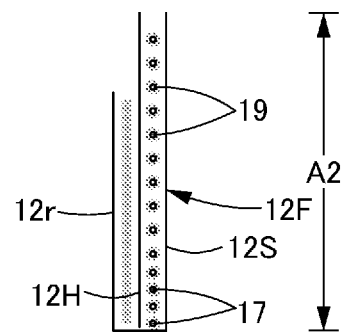

ABSORBENT ARTICLE

CROSS-REFERENCE TO RELATED APPLICATIONS

This application is the U.S. national stage application of International Application PCT/JP2018/008470, filed Mar. 6, 2018, which international application was published on Sep. 20, 2018, as International Publication WO 2018/168561 in the Japanese language. The International Application claims priority of Japanese Patent Application No. 2017-052394, filed Mar. 17, 2017. The international application and Japanese application are both incorporated herein by reference, in entirety.

TECHNICAL FIELD

The present invention relates to an absorbent article.

BACKGROUND ART

In general, an absorbent article includes an absorber, a top sheet covering a front surface side of the absorber, and a rising gather rising from both sides of the top sheet (see, for example, Patent Literatures 1 to 3). In such an absorbent article including a rising gather, movement of an excretion liquid such as urine temporarily present on the top sheet after excretion is blocked by the rising gather, and the excretion liquid stays between the rising gathers. Therefore, in particular, leakage of the excretion liquid from a periphery of a wearer's leg is prevented.

However, the excretion liquid may reach a tip of the rising gather depending on a wearer's posture or the amount of excretion. Therefore, when such a condition is likely to occur, the excretion liquid is likely to leak from a gap between the rising gather and a body surface.

In order to solve such a problem, Patent Literature 4 has proposed one having a side pocket on a lateral side of an absorber. The one described in Patent Literature 4 has a leak preventing wall protruding from a front surface side while covering an upper side of the side pocket, and the leak preventing wall has an introduction hole passing therethrough in a lower portion of an inner surface of the leak preventing wall. In this configuration, for example, when a large amount of excretion liquid is excreted vigorously and the liquid level of the excretion liquid on the top sheet reaches a certain level, the excretion liquid overflows into the leak preventing wall through the introduction hole of the leak preventing wall, flows into the side pocket on a lateral side of the absorber, and then is absorbed by the absorber. Therefore, the liquid level of the excretion liquid is unlikely to reach a tip of the rising gather.

However, the one described in Patent Literature 4 needs to form a hole in the sheet forming the leak preventing wall, and an excretion liquid does not overflow into the leak preventing wall through the introduction hole unless the liquid level of the excretion liquid reaches a certain level on the top sheet. Therefore, there is a possibility that the excretion liquid is unlikely to flow into the side pocket.

CITATION LIST

Patent Literature

Patent Literature 1: JP 2013-255849 A
Patent Literature 2: JP 2002-102282 A
Patent Literature 3: JP 2009-082358 A
Patent Literature 4: JP 2012-095790 A

SUMMARY OF INVENTION

Technical Problem

Therefore, a main object of the present invention is to facilitate a flow of an excretion liquid into a side pocket without forming a hole in a sheet with a simple structure, and to prevent leakage of the excretion liquid over a rising gather.

Solution to Problem

Representative aspects of the present invention solving the above problem are as follows.

<First Aspect>

An absorbent article including: an absorber; a top sheet covering a front surface side of the absorber; a liquid impervious sheet covering a back surface side of the absorber; and rising gathers rising from both sides of the top sheet, in which a side pocket extending in a front-back direction is disposed on a lateral side of the absorber, the side pocket is surrounded by a side cover portion reaching a back surface side of the absorber from above a side of the top sheet via an upper portion, an outer side, and a lower portion of the side pocket, a portion located above the side of the top sheet in the side cover portion includes a non-bonded portion not bonded to the top sheet and a bonded portion located on both front and back sides of the non-bonded portion, and a gap between the side cover portion and the top sheet in the non-bonded portion is open above the top sheet and toward the side pocket.

(Action and Effect)

In the present aspect, the side pocket surrounded by the side cover portion is disposed on a lateral side of the absorber, and a non-bonded portion not bonded to the top sheet and a bonded portion located on both front and back sides of the non-bonded portion are disposed in a portion located above a side of the top sheet in the side cover portion. A gap between the side cover portion and the top sheet in the non-bonded portion is open above the top sheet and toward the side pocket. As a result, with a simple structure not having a hole in the side cover portion but only having a non-bonded portion, an excretion liquid on the top sheet can flow into the side pocket regardless of the liquid level of the excretion liquid on the top sheet. The excretion liquid that has flowed into the side pocket is absorbed by an adjacent absorber.

<Second Aspect>

The absorbent article according to the first aspect, in which an elongated side cover elastic member is disposed in a front-back direction at least outside a portion located above the side pocket in a width direction in the side cover portion, and a portion having the side cover elastic member in the side cover portion is contracted in the front-back direction by a contraction force of the side cover elastic member.

(Action and Effect)

A portion having the side cover elastic member in the side cover portion is preferably contracted in a front-back direction because an upper portion of the side cover portion is lifted relative to a lower portion, the side pocket is secured largely, and an opening of the side pocket is easily opened toward the top sheet.

<Third Aspect>

The absorbent article according to the second aspect, in which a liquid impervious sheet covering a back surface side of the absorber is continuous along the side cover portion from a back surface side of the absorber to at least the side cover elastic member, or a cover liquid impervious sheet different from the liquid impervious sheet covering the back surface side of the absorber is continuous along the side cover portion from a portion overlapping with the liquid impervious sheet covering the back surface side of the absorber to at least the side cover elastic member.

(Action and Effect)

As a result, an excretion liquid in the side pocket does not permeate the side cover portion, and a waterproof property of the side cover portion can be secured securely.

<Fourth Aspect>

The absorbent article according to any one of the first to third aspects, in which the side cover portion is formed of a sheet material having a portion continuous from a back surface side of the absorber to a side of the top sheet via a lower portion, an outer side, and an upper portion of the side pocket, and the sheet material has a protruding portion protruding from the non-bonded portion and the bonded portion, and the protruding portion forms the rising gather.

(Action and Effect)

In this way, by forming a portion from the side cover portion to the rising gather with a continuous sheet material, a simpler structure can be formed. In addition, a gap between the side cover portion and the top sheet in a non-bonded portion is easily opened by a rising action of the rising gather.

<Fifth Aspect>

The absorbent article according to any one of the first to fourth aspects, in which an opening elastic member is disposed in a front-back direction at a position overlapping with at least the non-bonded portion on a back surface side of the non-bonded portion in a thickness direction, and at least a portion overlapping with the non-bonded portion in a thickness direction in the top sheet is contracted in the front-back direction by a contraction force of the opening elastic member.

(Action and Effect)

With such an opening elastic member, a top sheet side in the non-bonded portion contracts in a front-back direction and becomes shorter, and the size of the side cover portion in the front-back direction is excessive. Therefore, a gap between the side cover portion and the top sheet in the non-bonded portion is easily opened.

<Sixth Aspect>

The absorbent article according to any one of the first to fifth aspects, in which the non-bonded portion has a size of 15 to 100 mm in a front-back direction.

(Action and Effect)

When the size of the non-bonded portion in a front-back direction is too short, a gap between the side cover portion and the top sheet in the non-bonded portion tends to be narrow, and an excretion liquid may be unlikely to flow into the side pocket. When the size of the non-bonded portion in the front-back direction is too long, an opening of the side pocket is unfolded outward, and the side pocket may become smaller, or for example, in a case of an underpants-type disposable diaper, a foot may be easily caught by the non-bonded portion at the time of wearing. Therefore, the size of the non-bonded portion in the front-back direction is preferably within the above range.

<Seventh Aspect>

The absorbent article according to any one of the first to sixth aspects, in which a plurality of the non-bonded portions is disposed at intervals in a front-back direction in an intermediate portion in the front-back direction.

(Action and Effect)

By disposing a plurality of non-bonded portions in this way, the opening of the side pocket is unlikely to be unfolded outward while the sum of the sizes of the non-bonded portions in the front-back direction is large (equal to the size of the opening toward the top sheet in the side pocket). For example, in a case of an underpants-type disposable diaper, a situation that a foot is easily caught by the non-bonded portion at the time of wearing is unlikely to occur. In addition, even in a case where a large amount of excretion liquid locally flows depending on a difference in excretion position between men and women and a posture, the excretion liquid can flow into the side pocket in a wide range.

<Eighth Aspect>

The absorbent article according to any one of the first to seventh aspects, in which an inner space of the side pocket has a size of 5 mm or more in a width direction.

(Action and Effect)

In a usual case, the size of the side pocket in the width direction is preferably secured to this extent.

Advantageous Effects of Invention

As described above, according to the present invention, for example, an excretion liquid easily flows into the side pocket with a simple structure without forming a hole in the sheet advantageously.

BRIEF DESCRIPTION OF DRAWINGS

FIG. 3(*a*) is a 4-4 cross-sectional view of FIG. 1, and FIG. 3(*b*) is a 5-5 cross-sectional view of FIG. 1.

FIG. 16(*a*) is a 4-4 cross-sectional view of FIG. 15, and FIG. 16(*b*) is a 5-5 cross-sectional view of FIG. 15.

DESCRIPTION OF EMBODIMENTS

Figure 1:
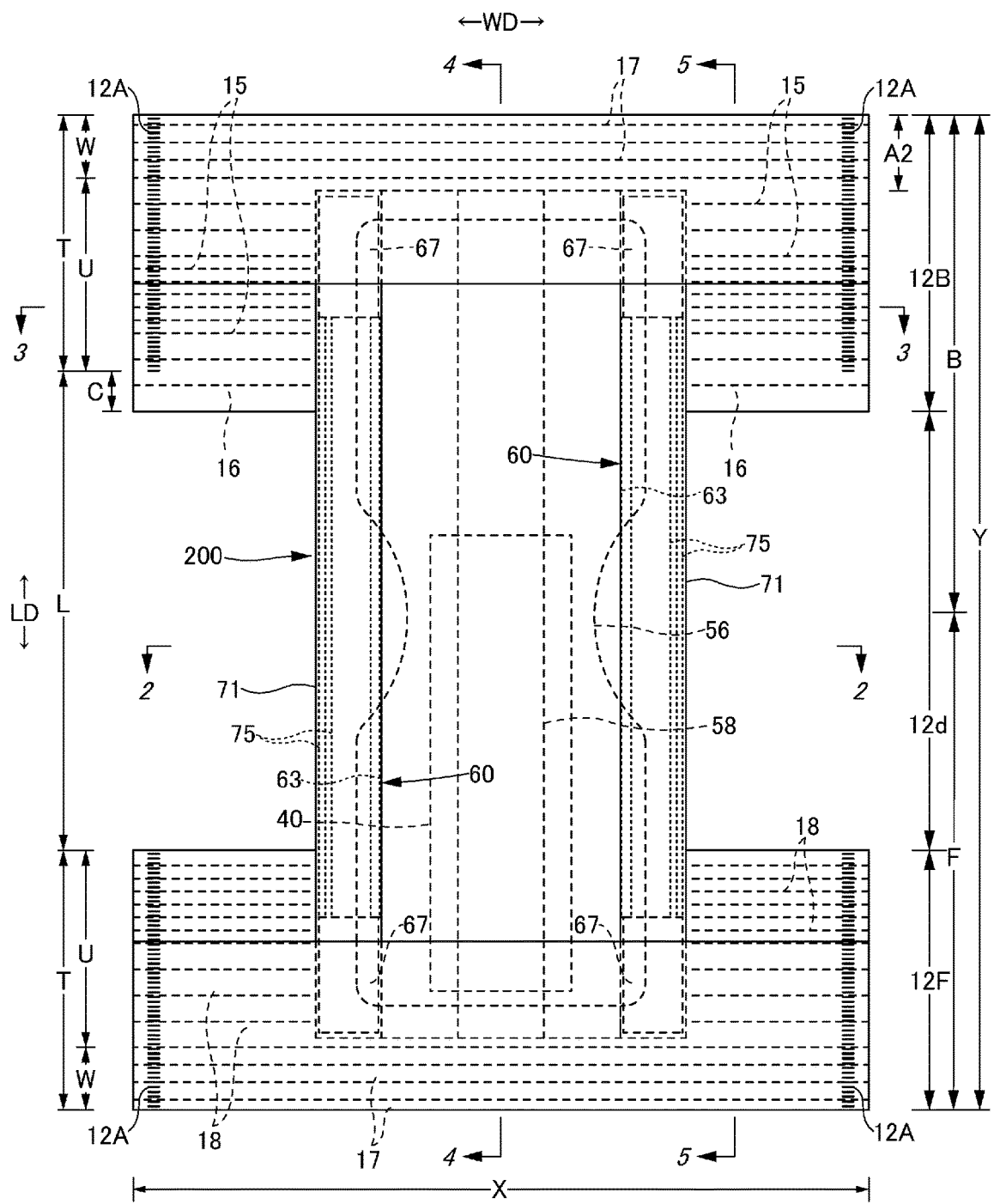
FIG. 1 is a plan view illustrating an inner surface of an underpants-type disposable diaper in an unfolded state.

Hereinafter, an embodiment of the present invention will be described in detail with reference to the attached drawings. A dotted pattern portion in the cross-sectional views illustrates an adhesive as a bonding means for bonding constituent members located on a front surface side and a back surface side, and is formed by applying a hot melt adhesive by solid application, bead application, curtain application, summit application, spiral application, pattern coating (transfer of a hot melt adhesive by a letterpress method), or the like. A fixing portion of an elastic member is formed, instead of this or in addition to this, by application to an outer peripheral surface of an elastic member by a comb gun, SureWrap application, or the like. Examples of the hot melt adhesive include an EVA-based agent, a pressure-sensitive adhesive rubber-based agent (elastomer-based agent), a polyolefin-based agent, and a polyester/polyamide-based agent, and these can be used without particular limitation. As a joining means for bonding constituent members, a means by material welding such as a heat sealing or ultrasonic sealing can also be used.

FIGS. 1 to 10 illustrate an example of an underpants-type disposable diaper. The underpants-type disposable diaper includes: a front outer body 12F constituting at least a lower torso portion of a front body F; a back outer body 12B constituting at least a lower torso portion of a back body B; and an inner body 200 disposed inside the outer bodies 12F and 12B so as to extend from the front outer body 12F to the back outer body 12B through a crotch portion. Both sides of the front outer body 12F and both sides of the back outer body 12B are bonded to each other to form a side seal portion 12A. As a result, an opening formed by the front and back end portions of the outer bodies 12F and 12B is a waist opening WO through which a wearer's torso passes, and a portion surrounded by lower edges of the outer bodies 12F and 12B and a side edge of the inner body 200 at both sides of the inner body 200 in a width direction is a leg opening LO through which a leg passes. The inner body 200 is a portion for absorbing and holding excrement such as urine, and the outer bodies 12F and 12B are portions for supporting the inner body 200 with respect to the body of a wearer. A reference numeral Y represents the maximum length of the diaper in an unfolded state (front-back direction length from an edge of a waist opening WO of the front body F to an edge of a waist opening WO of the back body B), and a reference numeral X represents the maximum width of the diaper in an unfolded state.

The underpants-type disposable diaper in the present embodiment has a lower torso region T defined as a front-back direction range (front-back direction range from the waist opening WO to the upper end of the leg opening LO) having the side seal portion 12A, and an intermediate region L defined as a front-back direction range of a portion forming the leg opening LO (between a front-back direction region having the side seal portion 12A of the front body F and a front-back direction region having the side seal portion 12A of the back body B). The lower torso region T can be divided into a "waist portion" W conceptually forming an edge portion of the waist opening and an "under-waist portion" U which is a portion lower than the waist portion W. Usually, in a case where the lower torso region T has a boundary in which a stretching stress in a width direction WD changes (for example, the thickness of an elastic member or the stretch rate thereof changes), a portion closer to the waist opening WO than the boundary closest to the waist opening WO is the waist portion W. In a case where there is no such a boundary, a portion closer to the waist opening WO than the absorber 56 or the inner body 200 is the waist portion W. The length of these portions in a front-back direction varies depending on the size of a product and can be appropriately determined. For example, the length of the waist portion W can be 15 to 40 mm, and the length of the under-waist portion U can be 65 to 120 mm. Meanwhile, both side edges of the intermediate region L are each narrowed in a substantially U shape or a curved shape so as to follow a periphery of a wearer's leg, and the wearer's leg passes therethrough. As a result, the underpants-type disposable diaper in an unfolded state has an approximately hourglass shape as a whole.

(Outer Body)

Figure 15:
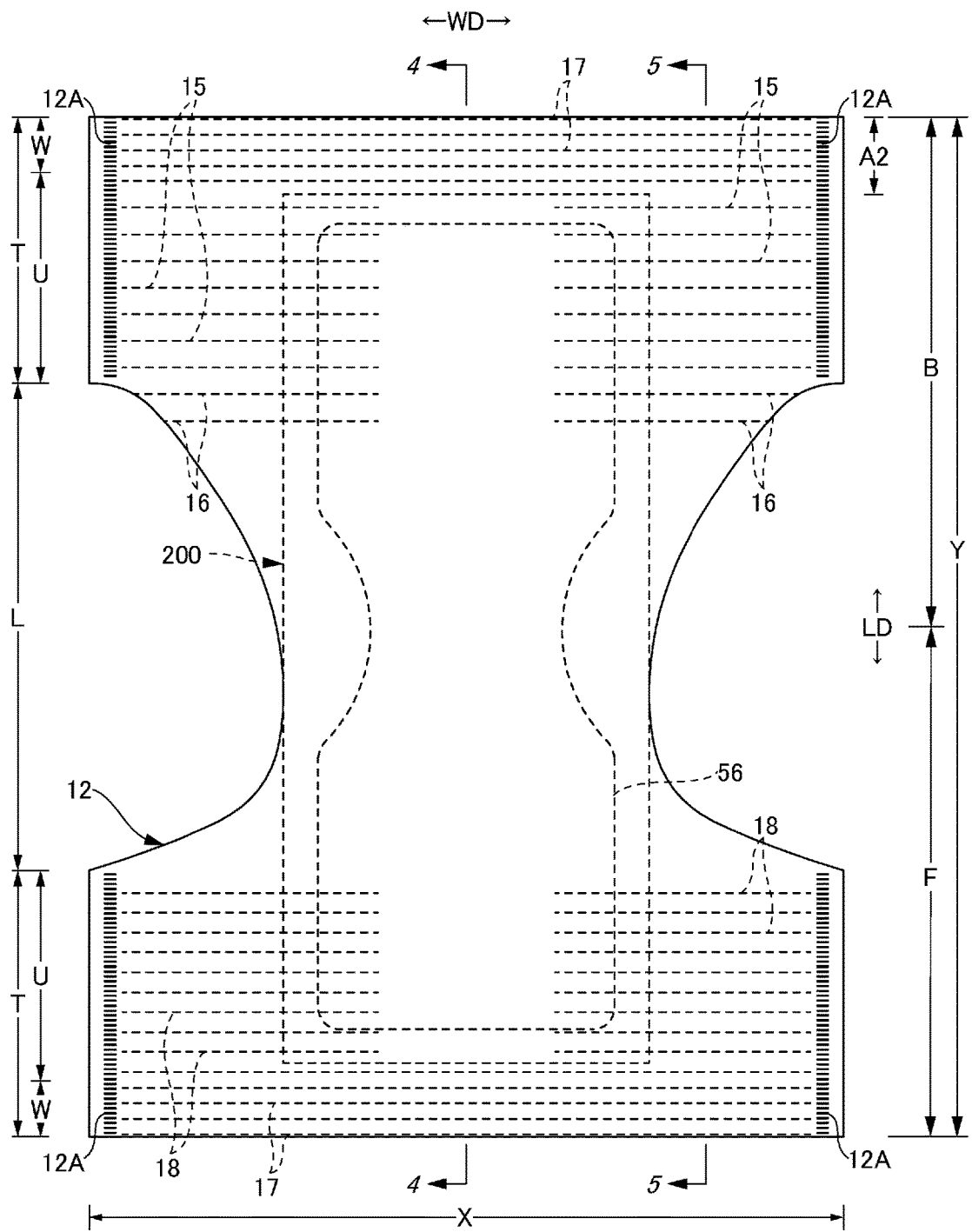
FIG. 15 is a plan view illustrating an outer surface of an underpants-type disposable diaper in an unfolded state.

The outer bodies 12F and 12B may be a continuous and integral outer body 12 passing through a crotch from the front body F to the back body B as illustrated in FIGS. 15 and 16. However, in the embodiments illustrated in FIGS. 1 to 13, the front outer body 12F which is a portion constituting at least a lower torso portion of the front body F and the back outer body 12B which is a portion constituting at least a lower torso portion of the back body B are included, and the front outer body 12F and the back outer body 12B are not continuous on a crotch side, and are separated from each other in a front-back direction LD. Its separation distance 12*d* can be about 150 to 250 mm, for example.

The outer bodies 12F and 12B have a lower torso portion which is a front-back direction range corresponding to the lower torso region T. In the present form embodiment, the front-back direction size of the back outer body 12B is longer than that of the front outer body 12F, and the front outer body 12F does not have a portion corresponding to the intermediate region L, but the back outer body 12B has a gluteal cover portion C extending from the lower torso region T to the intermediate region L side. Although not illustrated, in the front outer body 12F, an inguinal cover portion extending from the lower torso region T to the intermediate region L side may be disposed, or the inguinal cover portion may be disposed without a gluteal cover portion. Alternatively, in both the front outer body 12F and the back outer body 12B, it is not necessary to dispose a portion corresponding to the intermediate region L. In the illustrated embodiment, a lower edge of the gluteal cover portion C is formed into a linear shape in the width direction WD like a lower edge of the front outer body 12F, but may be formed into a curved shape so as to be closer to the waist opening side toward the outside in the width direction.

The front-back direction size of a side edge of the gluteal cover portion C only needs to be determined appropriately. However, when the size is too long, a corner of the side edge on the leg opening LO side may flutter, and an appearance and wearing feeling may be deteriorated. Therefore, the size is preferably 20 mm or less.

As illustrated in FIG. 3, the outer bodies 12F and 12B are formed by bonding an outer sheet layer 12S and an inner sheet layer 12H located on an outer side and an inner side of elastic members 15 to 18 described later, respectively, by a joining means such as a hot melt adhesive or welding. A sheet material forming the outer sheet layer 12S and a sheet material forming the inner sheet layer 12H may be a common single sheet material or may be individual sheet materials. That is, in the former case, the inner sheet layer 12H and the outer sheet layer 12S are formed of an inner portion and an outer portion of a single sheet of a sheet material folded back at an edge of the waist opening WO (which may be an edge on a crotch side) in a part or the whole of the outer body, respectively. Incidentally, in the former embodiment, the number of materials of the sheet material is small advantageously, and in the latter embodiment, positional deviation is unlikely to occur when the inner sheet layer 12H and the outer sheet layer 12S are bonded to each other. The illustrated embodiment corresponds to the latter, and the sheet material forming the inner sheet layer 12H extends only to an edge of the waist opening WO. However, the sheet material forming the outer sheet layer 12S goes around a waist side edge of the sheet material of the inner sheet layer 12H and folded back inward. A folded-back portion 12r extends so as to cover up to an upper portion of the waist side end portion of the inner body 200.

As the sheet material used for the outer sheet layer 12S and the inner sheet layer 12H, a known material can be used without particular limitation, but a nonwoven fabric is preferable. Examples of the nonwoven fabric include a nonwoven fabric formed of a synthetic fiber such as a polyolefin-based fiber including polyethylene and polypropylene, a polyester-based fiber, or a polyamide-based fiber, or a mixed fiber or a composite fiber using two or more kinds of these fibers. Furthermore, the nonwoven fabric may be manufactured by any processing. Examples of a processing method include a known method such as a spunlacing method, a spunbonding method, a thermal bond method, a melt blown method, a needle punching method, an air through method, and a point bond method. In a case where a nonwoven fabric is used, the nonwoven fabric preferably has a basis weight of about 10 to 30 g/m$^2$.

The outer bodies 12F and 12B preferably have a total basis weight of about 20 to 60 g/m$^2$.

(Stretchable Region/Non-Stretchable Region)

In the outer bodies 12F and 12B, in order to enhance fitting of a wearer to a lower torso, the elastic members 15 to 18 are disposed between the outer sheet layer 12S and the inner sheet layer 12H, and a stretchable region A2 that elastically expands and contracts in the width direction WD along with stretching and contracting of the elastic members 15 to 18 is formed. In the stretchable region A2, in a natural length state, the outer sheet layer 12S and the inner sheet layer 12H contract along with contraction of an elastic member to form wrinkles or pleats. When the elastic members 15 to 18 stretch in a longitudinal direction, it is possible to stretch the outer sheet layer 12S and the inner sheet layer 12H to a predetermined stretch rate at which the outer sheet layer 12S and the inner sheet layer 12H stretch without wrinkles. As the elastic members 15 to 18, in addition to an elongated elastic member (examples of illustration) such as a rubber thread, a known elastic member such as a belt-shaped member, a net-shaped member, or a film-shaped member can be used without particular limitation. As the elastic members 15 to 18, either a synthetic rubber or a natural rubber may be used.

For bonding the outer sheet layer 12S and the inner sheet layer 12H in the outer bodies 12F and 12B and fixing the elastic members 15 to 18 sandwiched therebetween, at least one of a hot melt adhesive by various application methods and a fixing means by material welding such as heat sealing or ultrasonic sealing can be used. When the entire surfaces of the outer bodies 12F and 12B are fixed rigidly, flexibility is impaired. Therefore, preferably, a portion other than a bonded portion of the elastic members 15 to 18 is not bonded or weakly bonded. In the illustrated embodiment, by applying a hot melt adhesive only to an outer peripheral surface of the elastic members 15 to 18 by an application means such as a comb gun or a SureWrap nozzle, and sandwiching the elastic members 15 to 18 between both the sheet layers 12S and 12H, the elastic members 15 to 18 are fixed to both the sheet layers 12S and 12H only with the hot melt adhesive applied to the outer peripheral surfaces of the elastic members 15 to 18, and both the sheet layers 12S and 12H are fixed to each other. The elastic members 15 to 18 can be fixed to the outer sheet layer 12S and the inner sheet layer 12H only at both end portions in a stretchable direction in a stretchable region.

The elastic members 15 to 18 in the illustrated embodiment will be described in more detail. Between the outer sheet layer 12S and the inner sheet layer 12H in the waist portion W of the outer bodies 12F and 12B, a plurality of waist portion elastic members 17 is attached at intervals in a front-back direction so as to be continuous across the entire width direction WD. One or more waist portion elastic members 17 disposed in a region adjacent to the under-waist portion U may overlap with the inner body 200, or may be disposed on both sides thereof in a width direction except for a central portion overlapping with the inner body 200 in the width direction. As the waist portion elastic member 17, it is preferable to dispose 3 to 22 rubber threads each having a thickness of 155 to 1880 dtex, particularly about 470 to 1240 dtex (in a case of a synthetic rubber, having a cross section area of 0.05 to 1.5 mm$^2$, particularly about 0.1 to 1.0 mm$^2$ in a case of a natural rubber) at intervals of 4 to 12 mm. A stretch rate of the waist portion W in the width direction WD due to this is preferably 150 to 400%, and particularly preferably about 220 to 320%. In the waist portion W, all of the waist portion elastic members 17 in the front-back direction LD do not have to have the same thickness and the same stretch rate. For example, the thickness and the stretch rate of the elastic member 17 may be different between an upper portion and a lower portion of the waist portion W.

Between the outer sheet layer 12S and the inner sheet layer 12H in the under-waist portion U of the outer bodies 12F and 12B, a plurality of under-waist portion elastic members 15 and 18 formed of an elongated elastic member is disposed at intervals in a front-back direction.

As the under-waist portion elastic members 15 and 18, it is preferable to dispose 5 to 30 rubber threads each having a thickness of 155 to 1880 dtex, particularly about 470 to 1240 dtex (in a case of a synthetic rubber, having a cross section area of 0.05 to 1.5 mm$^2$, particularly about 0.1 to 1.0 mm$^2$ in a case of a natural rubber) at intervals of 1 to 15 mm, particularly 3 to 8 mm. A stretch rate of the under-waist portion U in the width direction WD due to this is preferably 200 to 350%, and particularly preferably about 240 to 300%.

Between the outer sheet layer 12S and the inner sheet layer 12H in the gluteal cover portion C of the back outer body 12B, a cover portion elastic member 16 formed of an elongated elastic member is attached.

As the cover portion elastic member 16, it is preferable to dispose one or more rubber threads each having a thickness of 155 to 1880 dtex, particularly about 470 to 1240 dtex (in a case of a synthetic rubber, having a cross section area of 0.05 to 1.5 mm$^2$, particularly about 0.1 to 1.0 mm$^2$ in a case of a natural rubber) at intervals in a front-back direction. A stretch rate of the gluteal cover portion C in the width direction WD due to this is preferably 150 to 300%, and particularly preferably about 180 to 260%.

In a case where an inguinal cover portion is disposed in the front outer body 12F, the cover portion elastic member can be disposed similarly.

In a case where the elastic members 15, 16, and 18 are disposed in a front-back direction range having the absorber 56 like the under-waist portion U and the gluteal cover portion C in the illustrated embodiment, in order to prevent contraction of a part or the whole of the elastic members 15, 16, and 18 in the width direction WD of the absorber 56, a width direction intermediate portion including a part or the whole of a portion overlapping with the absorber 56 in the width direction WD (preferably including the whole of the inner and outer bonded portions 201 and 202) is set as a non-stretchable region A1, and both sides thereof in the width direction are set as a stretchable region A2. The waist portion W is preferably set as the stretchable region A2 over the entire width direction WD. However, like the under-waist portion U, the waist portion W may have the non-stretchable region A1 in an intermediate portion in the width direction.

Figure 4:
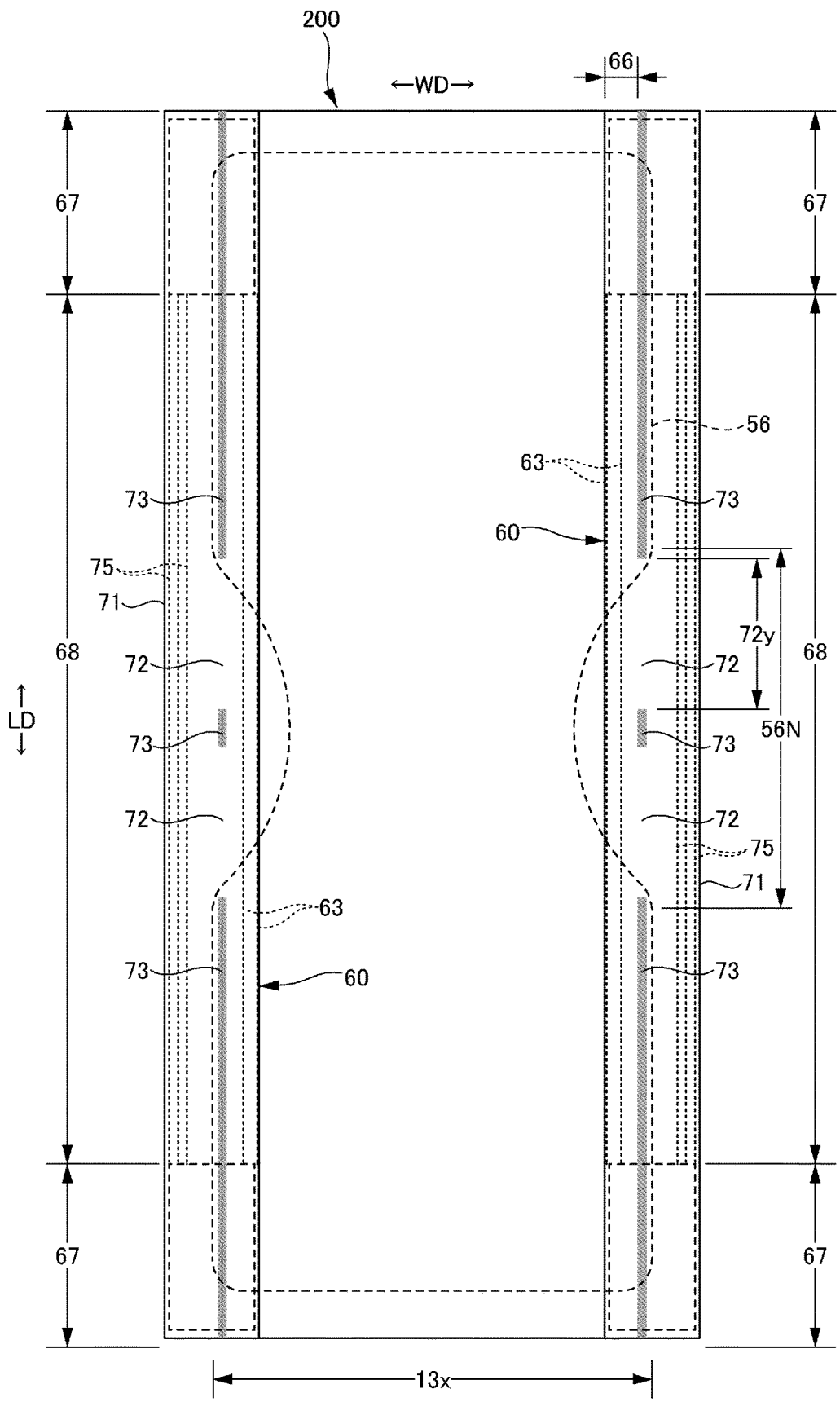
FIG. 4 is a plan view illustrating an outer surface of an inner body in an unfolded state.

The stretchable region A2 and the non-stretchable region A1 can be formed by supplying elastic members 15 to 17 and 18 between the inner sheet layer 12H and the outer sheet layer 12S, fixing the elastic members 15, 16, and 18 in at least both end portions in a stretchable direction in the stretchable region A2 through a hot melt adhesive without fixing the elastic members 15, 16, and 18 in a region set as the non-stretchable region A1, and cutting the elastic members 15, 16, and 18 at one place in a width direction intermediate portion in the region set as the non-stretchable region A1 by pressing and heating or cutting almost the whole of the elastic members 15, 16, and 18 finely by pressing and heating to leave elasticity in the stretchable region A2 and destroying elasticity in the non-stretchable region A1. In the former case, as illustrated in FIG. 4, in the non-stretchable region A1, a cutting residue continuous from the elastic members 15, 16, and 18 in the stretchable region A2 remains between the outer sheet layer 12S and the inner sheet layer 12H while being contracted alone as an unnecessary elastic member 19 to a natural length. In the latter case, although not illustrated, a cutting residue continuous from the elastic members 15, 16, and 18 in the stretchable region A2 and a cut piece of an elastic member not continuous from the elastic members 15, 16, and 18 in both the stretchable regions A2 remain between the outer sheet layer 12S and the inner sheet layer 12H while being contracted alone as the unnecessary elastic member 19 to a natural length.

(Cover Nonwoven Fabric)

In an outer two-division type underpants-type disposable diaper, the inner body 200 is exposed between the front outer body 12F and the back outer body 12B. Therefore, in order to prevent the liquid impervious sheet 11 from being exposed to a back surface of the inner body 200, the outer two-division type underpants-type disposable diaper includes a cover nonwoven fabric 13 covering the back surface of the inner body 200 from a portion between the front outer body 12F and the inner body 200 to a portion between the back outer body 12B and the inner body 200. As the cover nonwoven fabric 13, an appropriate nonwoven fabric such as an imperforated nonwoven fabric having no hole passing therethrough from the front to the back or a perforated nonwoven fabric having many holes passing therethrough from the front to the back at intervals can be used.

The type of a fiber of the cover nonwoven fabric 13 and a method for processing in bonding (interlacing) the fibers are not particularly limited, and similar ones to those of materials of the outer bodies 12F and 12B can be appropriately selected. However, it is desirable to use an air through nonwoven fabric. In this case, the basis weight is preferably 20 to 40 g/m$^2$ and the thickness is preferably 0.3 to 1.0 mm.

Figure 2:
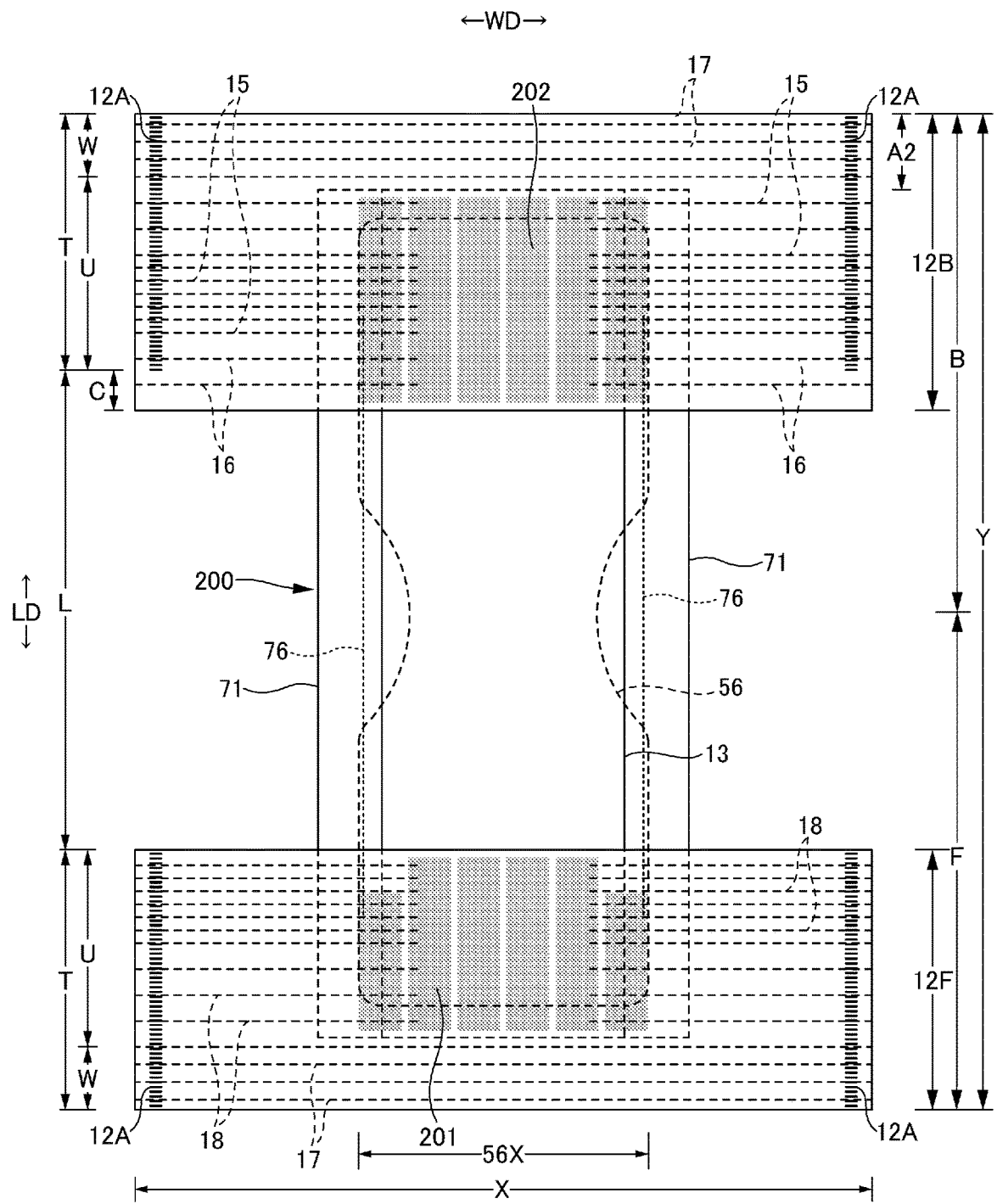
FIG. 2 is a plan view illustrating an outer surface of an underpants-type disposable diaper in an unfolded state.
Figure 8:
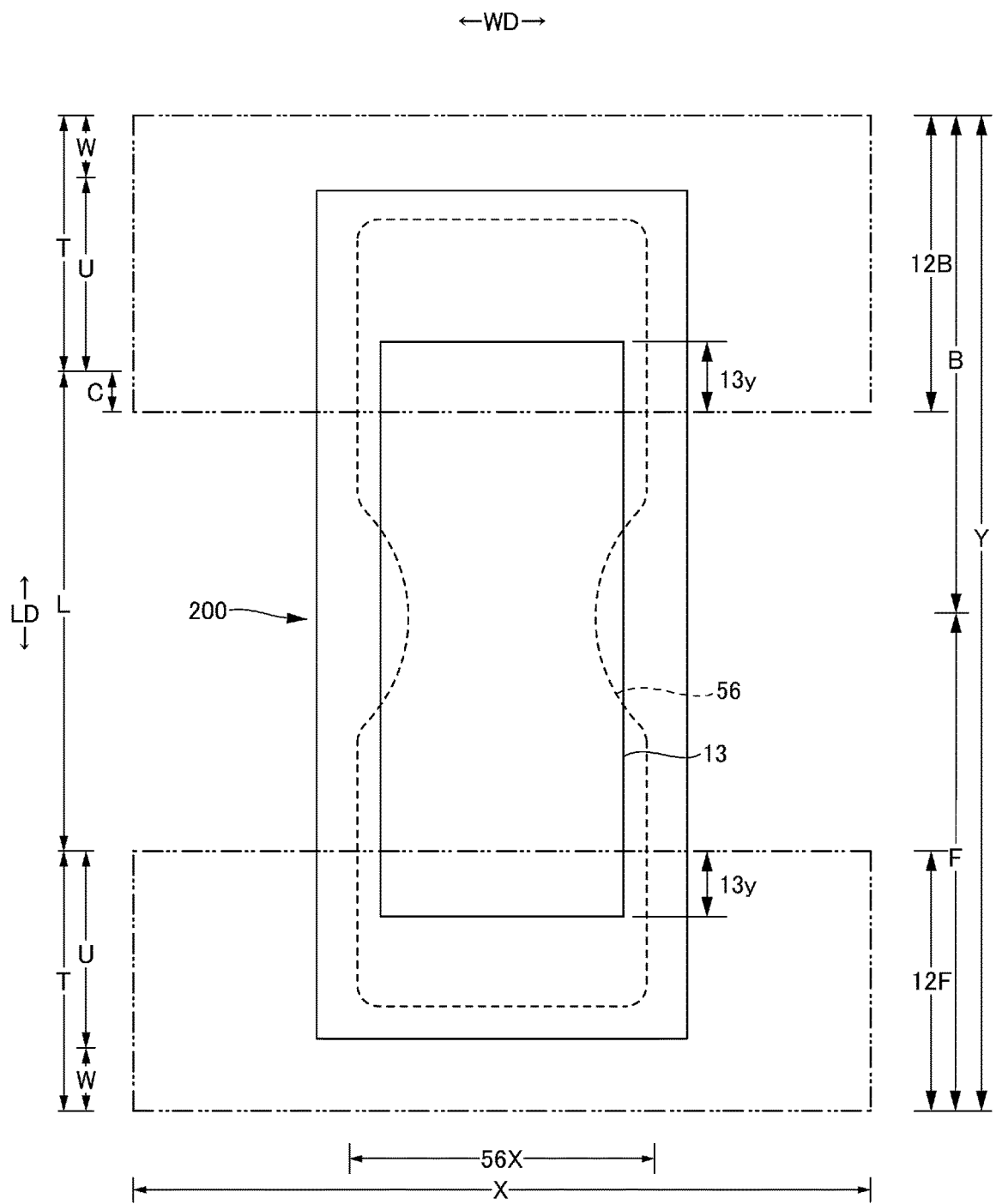
FIG. 8 is a plan view illustrating an outer surface of an inner body in an unfolded state together with an outline of an outer body.

The front-back direction range of the cover nonwoven fabric 13 is not particularly limited, and as illustrated in FIGS. 2, 3, and 8, may extend in the front-back direction LD over the entire region from a front end to a back end of the inner body 200. As illustrated in FIG. 8, the front-back direction range of the cover nonwoven fabric 13 may extend in the front-back direction LD from a front-back direction intermediate position of a region where the front outer body 12F and the inner body 200 overlap with each other to a front-back direction intermediate position of a region where the back outer body 12B and the inner body 200 overlap with each other. In the case of the embodiment illustrated in FIG. 8, a front-back direction length 13y of an overlapping portion between the cover nonwoven fabric 13 and the front outer body 12F and a front-back direction length 13y of an overlapping portion between the cover nonwoven fabric 13 and the back outer body 12B can be appropriately determined, but can be each about 20 to 40 mm in a usual case.

The width direction range of the cover nonwoven fabric 13 is a range in which a back surface exposed portion of the liquid impervious sheet 11 can be concealed. For this reason, in the illustrated embodiment, the liquid impervious sheet 11 is exposed between bases of side cover portions 71 described later. Therefore, the cover nonwoven fabric 13 is disposed so as to cover a width direction range from a back surface side of a base portion of one of the side cover portions 71 to a back surface side of a base portion of the other of the side cover portions 71.

(Inner and Outer Bonded Portion)

A back surface of the inner body 200 and the outer bodies 12F and 12B are bonded to each other at the inner and outer bonded portions 201 and 202. Fixing at the inner and outer bonded portions 201 and 202 can be performed by a bonded means by material welding such as heat sealing or ultrasonic sealing, or a hot melt adhesive.

(Inner Body)

The inner body 200 can adopt an arbitrary shape, but is rectangular in the illustrated embodiment. As illustrated in FIGS. 3 to 6, the inner body 200 includes a top sheet 30 to become a body side, the liquid impervious sheet 11, and an absorbent element 50 interposed therebetween, and is a main unit section having an absorption function. A reference numeral 40 represents an intermediate sheet (second sheet) disposed between the top sheet 30 and the absorbent element 50 in order to rapidly transfer a liquid that has passed through the top sheet 30 to the absorbent element 50. A reference numeral 60 represents a rising gather 60 extending so as to come into contact with a body of a wearer from both sides of the inner body 200 in order to prevent leakage of excrement into both sides of the inner body 200.

(Top Sheet)

The top sheet 30 transmits a liquid, and examples thereof include a perforated or imperforated nonwoven fabric and a porous plastic sheet. Among these materials, the nonwoven fabric is not particularly limited concerning a raw material fiber thereof. Examples thereof include a synthetic fiber such as a polyolefin-based fiber including polyethylene and polypropylene, a polyester-based fiber, or a polyamide-based fiber, a regenerated fiber such as rayon or cupra, a natural fiber such as cotton, and a mixed fiber and a composite fiber in which two or more kinds of these fibers are used. Furthermore, the nonwoven fabric may be manufactured by any processing. Examples of a processing method include a known method such as a spunlacing method, a spunbonding method, a thermal bond method, a melt blown method, a needle punching method, an air through method, and a point bond method. For example, if flexibility and drapeability are demanded, a spunbonding method and a spunlacing method are preferable processing methods. If bulkiness and softness are demanded, an air through method, a point bond method, and a thermal bond method are preferable processing methods.

The top sheet 30 may be formed of a single sheet or a stacked sheet obtained by bonding two or more sheets to each other. Similarly, the top sheet 30 may be formed of one sheet or two or more sheets in a plane direction.

Both side portions of the top sheet 30 may be folded back to a back surface side at a side edge of the absorbent element 50 or may be projected from the side edge of the absorbent element 50 to a lateral side without being folded back.

For the purpose of preventing positional deviation with respect to a back surface side member or the like, it is desirable that the top sheet 30 is fixed to a member adjacent to the back surface side by a bonding means by material welding such as heat sealing or ultrasonic sealing, or a hot melt adhesive. In the illustrated embodiment, the top sheet 30 is fixed to a surface of an intermediate sheet 40 and a surface of a portion located on a front surface side of the absorber 56 in a wrapping sheet 58 with a hot melt adhesive applied to a back surface thereof.

(Intermediate Sheet)

In order to quickly transfer a liquid that has passed through the top sheet 30 to the absorber, it is possible to dispose the intermediate sheet (also referred to as "second sheet") 40 having a higher liquid transmission rate than the top sheet 30. The intermediate sheet 40 is used in order to rapidly transfer a liquid to the absorber to enhance absorption performance of the absorber, and to prevent a "returning" phenomenon of the absorbed liquid from the absorber. The intermediate sheet 40 can be omitted.

Examples of the intermediate sheet 40 include a similar material to that of the top sheet 30, a spunlaced nonwoven fabric, a spunbonded nonwoven fabric, an SMS nonwoven fabric, a pulp nonwoven fabric, a mixed sheet of pulp and rayon, a point bonded material, and crepe paper. In particular, an air through nonwoven fabric is preferable because of being bulky. As the air through nonwoven fabric, a composite fiber having a core-sheath structure is preferably used. In this case, a resin used for the core may be polypropylene (PP) but is preferably polyester (PET) having high rigidity. The basis weight is preferably 17 to 80 $g/m^2$, and more preferably 25 to 60 $g/m^2$. A raw material fiber of the nonwoven fabric preferably has a thickness of 2.0 to 10 dtex. In order to make the nonwoven fabric bulky, as mixed fibers of all or some of raw material fibers, eccentric fibers having no core in the center, hollow fibers, eccentric and hollow fibers are also preferably used.

The intermediate sheet 40 in the illustrated embodiment is disposed at the center so as to be shorter than the width of the absorber 56, but may be disposed over the maximum width. The front-back direction length of the intermediate sheet 40 may be the same as the maximum length of a diaper, may be the same as the length of the absorbent element 50, or may be within a short length range centered on a liquid receiving region.

For the purpose of preventing positional deviation with respect to a back surface side member or the like, it is desirable that the intermediate sheet 40 is fixed to a member adjacent to the back surface side by a bonding means by material welding such as heat sealing or ultrasonic sealing, or a hot melt adhesive. In the illustrated embodiment, the intermediate sheet 40 is fixed to a surface of a portion located on a front surface side of the absorber 56 in the wrapping sheet 58 with a hot melt adhesive applied to a back surface thereof.

(Liquid Impervious Sheet)

A material of the liquid impervious sheet 11 is not particularly limited, but examples thereof include a plastic film formed of a polyolefin-based resin such as polyethylene or polypropylene, a laminated nonwoven fabric having a plastic film disposed on a surface of a nonwoven fabric, and a stacked sheet obtained by superposing and joining a nonwoven fabric or the like to a plastic film. For the liquid impervious sheet 11, it is preferable to use a liquid impervious and moisture permeable material favorably used from a viewpoint of preventing stuffiness. As a moisture permeable plastic film, a microporous plastic film obtained by kneading an inorganic filler in a polyolefin-based resin such as polyethylene or polypropylene, molding a sheet, and then stretching the sheet in a monoaxial or biaxial direction is widely used. In addition, a nonwoven fabric using a micro denier fiber, a nonwoven fabric that has reinforced leakproofness by reducing a space between fibers by applying heat and pressure, and a sheet that has become liquid impervious without using a plastic film by a method for applying a super absorbent polymer, a hydrophobic resin, or a water repellent agent can be used as the liquid impervious sheet 11. However, it is desirable to use a resin film in order to obtain sufficient bonding strength at the time of bonding to the cover nonwoven fabric 13 described later through a hot melt adhesive.

The liquid impervious sheet 11 may have a width housed in a back surface side of the absorbent element 50 as illustrated in the drawing, or may go around both sides of the absorbent element 50 and extend to both sides of a side surface of the top sheet 30 of the absorbent element 50 in order to enhance leakproofness. The extending portion appropriately has a width of about 5 to 20 mm on each of the left and the right.

On an inner side of the liquid impervious sheet 11, in particular, on a side surface of the absorber 56, an excretion indicator that changes a color due to absorption of a liquid can be disposed.

(Absorbent Element)

The absorbent element 50 includes the absorber 56 and the wrapping sheet 58 wrapping the entire absorber 56. The wrapping sheet 58 can also be omitted.

(Absorber)

The absorber 56 can be formed by an assembly of fibers. As this fiber assembly, in addition to those obtained by accumulating short fibers such as fluff pulps or synthetic fibers, a filament assembly obtained by opening a tow (fiber bundle) of synthetic fibers such as cellulose acetate as necessary can also be used. In a case where fluff pulps or short fibers are accumulated, a fiber basis weight may be, for example, about 100 to 300 $g/m^2$. In a case of a filament assembly, a fiber basis weight may be, for example, about 30 to 120 $g/m^2$. In a case of a synthetic fiber, a fineness is, for example, 1 to 16 dtex, preferably 1 to 10 dtex, and more preferably 1 to 5 dtex. In a case of a filament assembly, the filament may be formed of non-crimped fibers but is preferably formed of crimped fibers. The degree of crimp of the crimped fibers may be, for example, about 5 to 75, preferably 10 to 50, and more preferably 15 to 50 per 2.54 cm. A uniformly crimped fiber is often used. In the absorber 56, super absorbent polymer particles are preferably dispersed and held.

Figure 7:
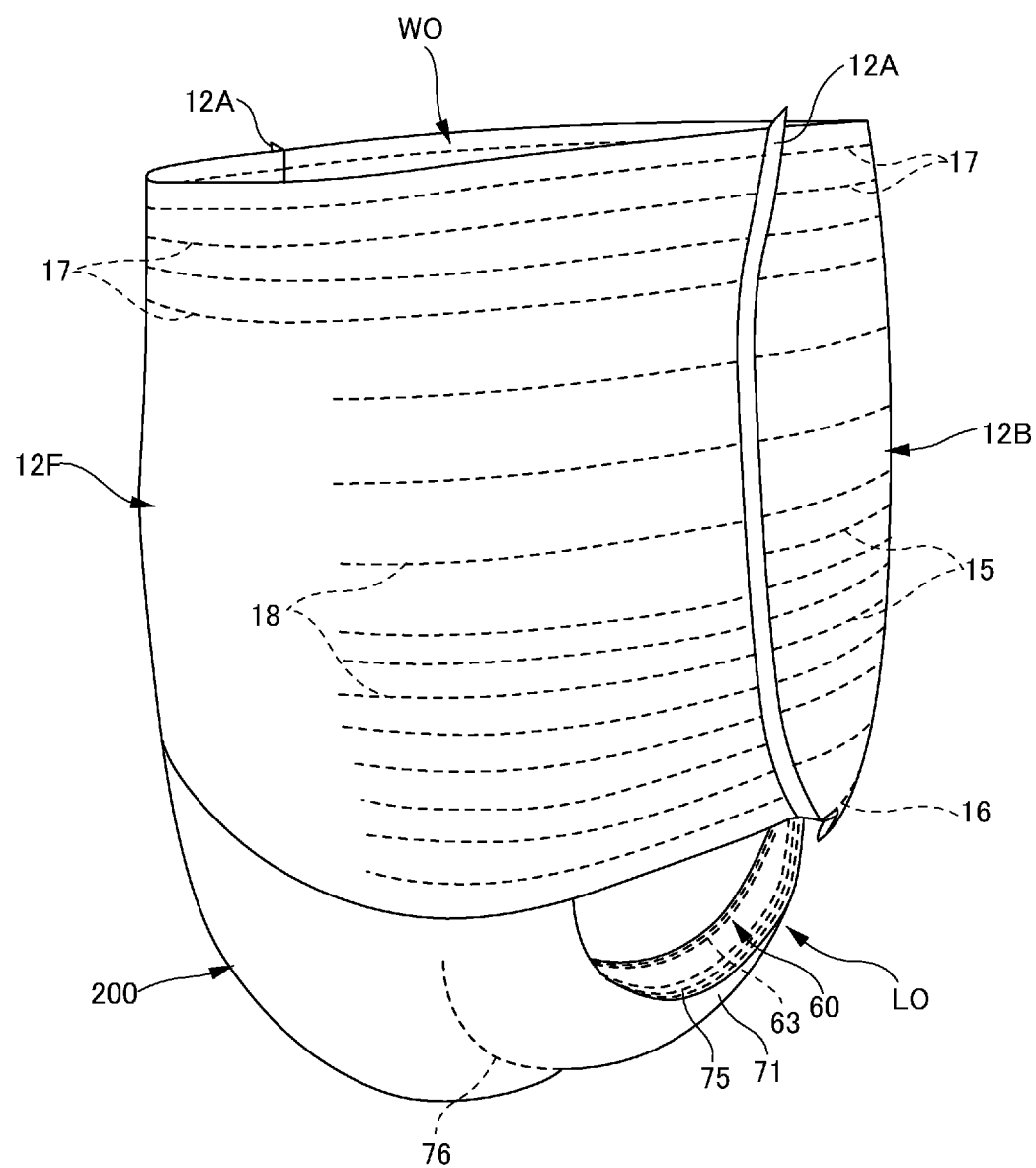
FIG. 7 is a perspective view of an underpants-type disposable diaper (hole is omitted).

The absorber 56 may have a rectangular shape. However, as illustrated in FIGS. 1, 7, and the like, the absorber 56 preferably has an hourglass shape having a narrower portion 56N with a narrower width than both sides in a front-back direction in an intermediate portion in the front-back direction.

The size of the absorber 56 can be determined appropriately as long as the absorber 56 extends to the front, back, left, and right of a ureteral port position. However, the absorber 56 preferably extends to peripheral edges of the inner body 200 or the vicinity thereof in the front-back direction LD and the width direction WD. Note that a reference numeral 56X represents the maximum width of the absorber 56.

(Super Absorbent Polymer Particles)

The absorber 56 may contain super absorbent polymer particles partially or entirely. The super absorbent polymer particles include "powder" in addition to "particles". As super absorbent polymer particles 54, those used for this type of disposable diaper can be used as they are. For example, when sieving using a standard sieve of 500 μm (JIS Z8801-1: 2006) (shake for five minutes) is performed, particles in which a ratio of particles remaining on the sieve is 30% by weight or less are desirable. When sieving using a standard sieve of 180 μm (JIS Z8801-1: 2006) (shake for five minutes) is performed, particles in which a ratio of particles remaining on the sieve is 60% by weight or more are desirable.

A material of the super absorbent polymer particles can be used without particular limitation, but those having a water absorption capacity of 40 g/g or more are preferable. Examples of the super absorbent polymer particles include a starch-based material, a cellulose-based material, and a synthetic polymer-based material. A starch-acrylic acid (salt) graft copolymer, a saponified product of a starch-acrylonitrile copolymer, a cross-linked product of sodium carboxymethyl cellulose, an acrylic acid (salt) polymer, or the like can be used. As the shapes of the super absorbent polymer particles, a usually used particulate material shape is suitable, but other shapes can also be used.

As the super absorbent polymer particles, those having a water absorption rate of 70 seconds or less, particularly 40 seconds or less are suitably used. When the water absorption rate is too slow, so-called returning that a liquid supplied into the absorber 56 returns out of the absorber 56 tends to occur.

As the super absorbent polymer particles, those having a gel strength of 1000 Pa or more are suitably used. This makes it possible to effectively suppress sticky feeling after liquid absorption even in a case of using the bulky absorber 56.

The basis weight of the super absorbent polymer particles can be appropriately determined depending on the absorption amount required for an application of the absorber 56. Therefore, the basis weight can be 50 to 350 g/m$^2$ although this cannot be applied generally. The basis weight of a polymer of less than 50 g/m$^2$ makes it difficult to secure the absorption amount. The basis weight of more than 350 g/m$^2$ saturates an effect.

The spray density or the spray amount of the super absorbent polymer particles in a planar direction of the absorber 56 can be changed if necessary. For example, the spray amount at a liquid excretion site can be larger than that at another site. When a gender difference is considered, the spray density (amount) at a front side can be increased for men, and the spray density (amount) at a central portion can be increased for women. It is also possible to locally dispose a portion where no polymer is present (for example, in a spot shape) in a planar direction of the absorber 56.

(Wrapping Sheet)

In a case where the wrapping sheet 58 is used, as a material thereof, tissue paper, particularly, crepe paper, a nonwoven fabric, a polylaminated nonwoven fabric, or a sheet with small holes can be used. However, it is desirable that the wrapping sheet 58 is a sheet from which super absorbent polymer particles do not escape. In a case where a nonwoven fabric is used instead of crepe paper, a hydrophilic SMS nonwoven fabric (SMS, SSMMS, or the like) is particularly suitable, and polypropylene, a polyethylene/polypropylene composite material, or the like can be used as a material thereof. A nonwoven fabric having a basis weight of 5 to 40 g/m$^2$, particularly of 10 to 30 g/m$^2$ is desirable.

A wrapping form of the wrapping sheet 58 can be determined appropriately. However, an embodiment is preferable in which the wrapping sheet 58 is wound around the absorber 56 cylindrically so as to surround front and back surfaces and both side surfaces of the absorber 56, the front and back end portions of the wrapping sheet 58 are caused to project from the front and back of the absorber 56, and a wound and overlapping portion and an overlapping portion of the front and back projecting portions are bonded by a bonding means such as a hot melt adhesive or material welding from viewpoints of ease of manufacture, prevention of leakage of the super absorbent polymer particles from front and back edges, and the like.

(Side Pocket)

Figure 5:
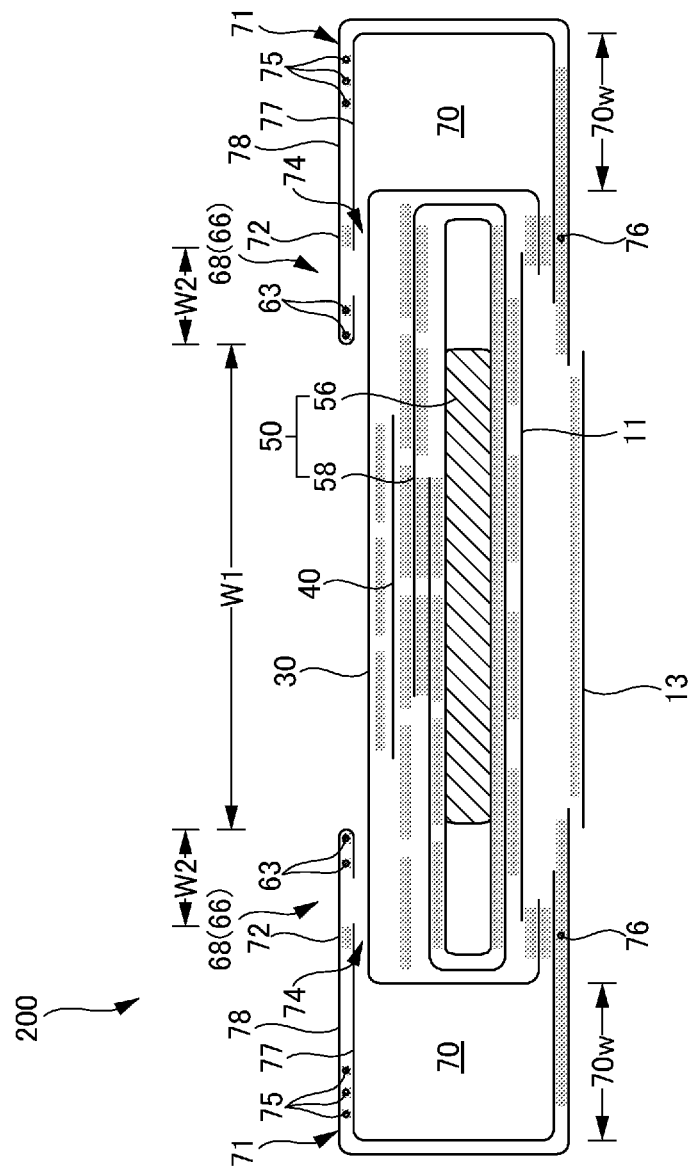
FIG. 5 is a 2-2 cross-sectional view of FIG. 1.
Figure 6:
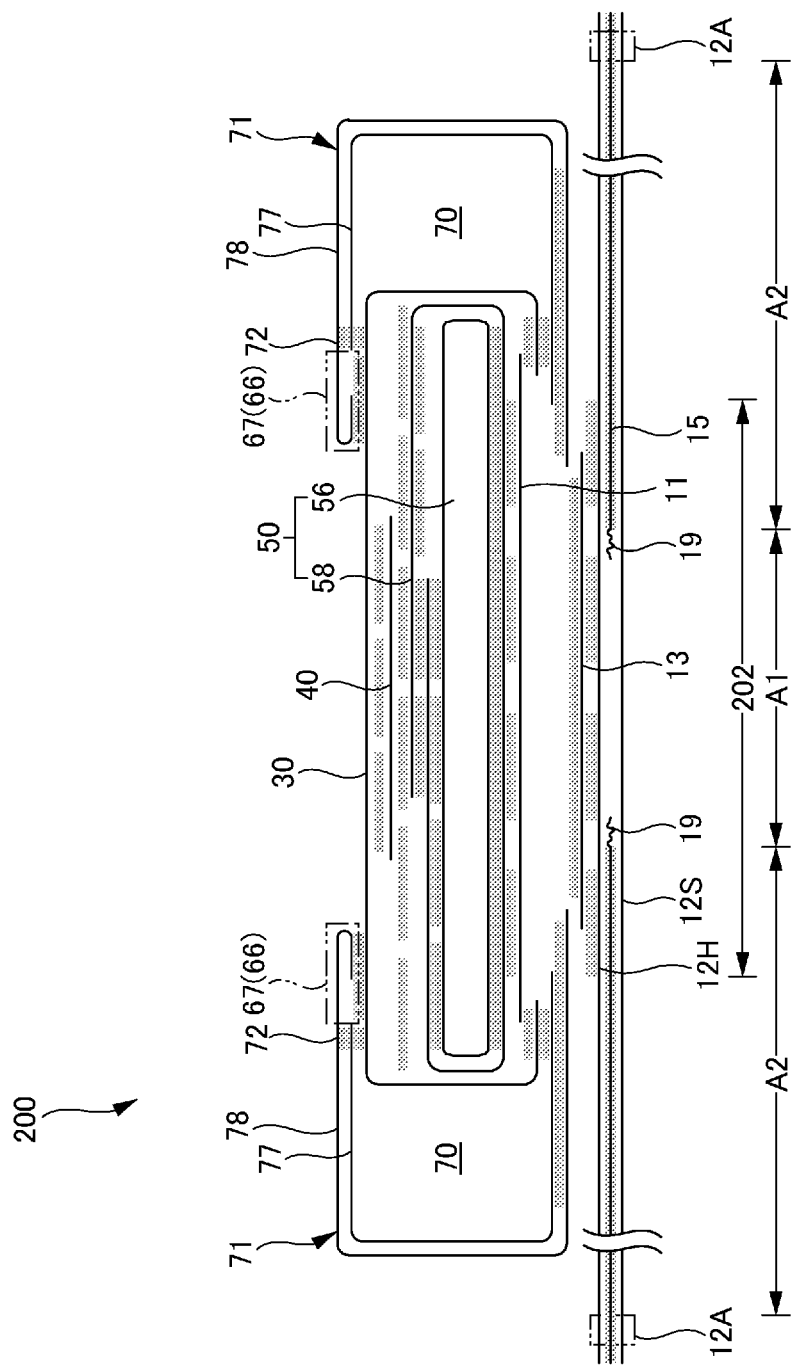
FIG. 6 is a 3-3 cross-sectional view of FIG. 1.
Figure 9:
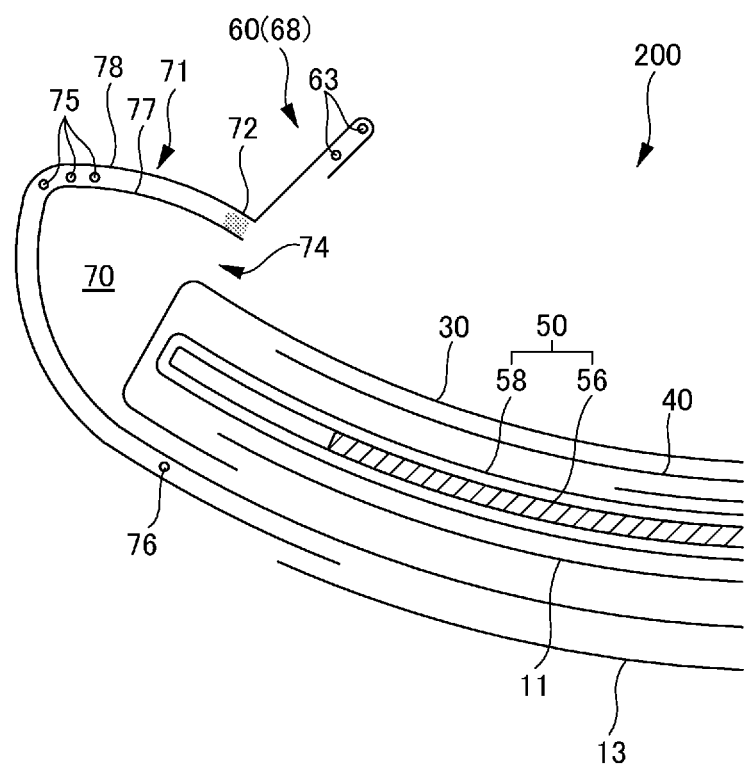
FIG. 9 is a cross-sectional view of a main part illustrating a side pocket portion in a mounted state.
Figure 10:
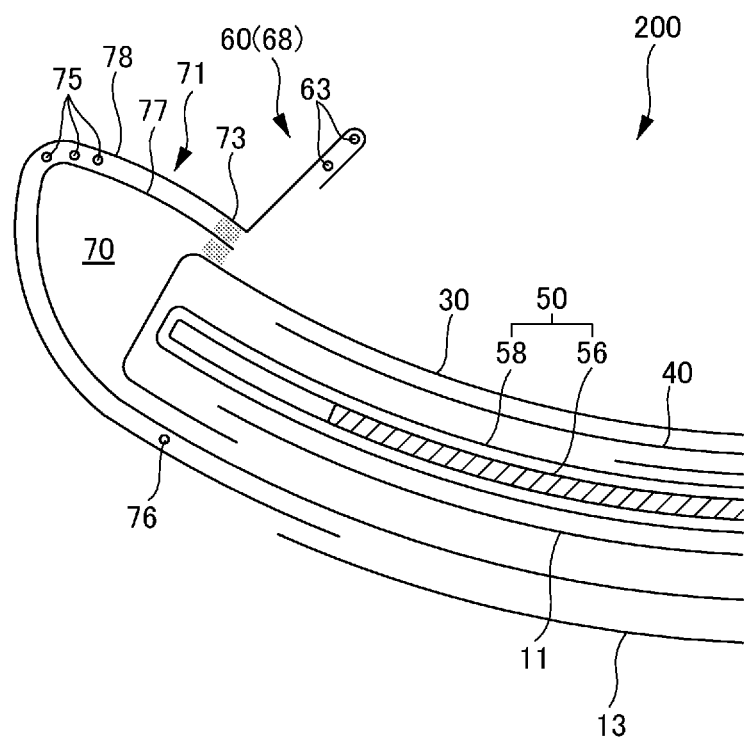
FIG. 10 is a cross-sectional view of a main part illustrating a side pocket part in a mounted state.

As illustrated in FIGS. 5 and 6, a side pocket 70 extending in the front-back direction LD is disposed on a lateral side of the absorber 56. The side pocket 70 is surrounded by a side cover portion 71 reaching a back surface side of the absorber 56 from above a side of the top sheet 30 via an upper portion, an outer side, and a lower portion of the side pocket 70. As illustrated in FIGS. 4 to 6, a portion located above a side of the top sheet 30 in the side cover portion 71 has a non-bonded portion 72 not bonded to the top sheet 30, and a bonded portion 73 located on both front and back sides of the non-bonded portion 72 and bonded to the top sheet 30. A gap 74 between the side cover portion 71 and the top sheet 30 in the non-bonded portion 72 is open above the top sheet 30 and toward the side pocket 70. FIGS. 9 and 10 illustrate a mounted state. As a result, with a simple structure not having a hole in the side cover portion 71 but only having a non-bonded portion 72, an excretion liquid on the top sheet 30 can flow into the side pocket 70 regardless of the liquid level of the excretion liquid on the top sheet 30. The excretion liquid that has flowed into the side pocket 70 is absorbed by an adjacent absorber 56.

The size of an inner space of the side pocket 70 can be appropriately determined. However, a size 70w thereof in the width direction WD is preferably 5 mm or more, and particularly preferably 5 to 40 mm, and the size thereof in the front-back direction LD is preferably about 80 to 100% of the maximum length of the absorber 56.

As in the illustrated example, the non-bonded portion 72 is preferably disposed in an intermediate portion in the front-back direction LD, particularly preferably in a crotch portion. Only one non-bonded portion 72 may be disposed. However, a plurality of the non-bonded portions 72 is preferably disposed at intervals in the front-back direction LD as illustrated in FIG. 4. By disposing the plurality of non-bonded portions 72, the opening of the side pocket 70 is unlikely to be spread outward while the sum of sizes 72y of the non-bonded portions 72 in the front-back direction LD is large (equal to the size of the opening toward the top sheet 30 in the side pocket 70). For example, in a case of an underpants-type disposable diaper, a situation that a foot is easily caught by the non-bonded portion 72 at the time of wearing is unlikely to occur.

The size of the non-bonded portion 72 can be determined appropriately, but the size 72y of the non-bonded portion 72 in the front-back direction LD is preferably 15 to 100 mm. When the size 72y of the non-bonded portion 72 in the front-back direction LD is too short, the gap 74 between the side cover portion 71 and the top sheet 30 in the non-bonded portion 72 tends to be narrow, and an excretion liquid may be unlikely to flow into the side pocket 70. When the size 72y of the non-bonded portion 72 in the front-back direction LD is too long, an opening of the side pocket 70 is spread outward, and the side pocket 70 may become smaller, or for example, in a case of an underpants-type disposable diaper, a foot may be easily caught by the non-bonded portion 72 at the time of wearing. Therefore, the size 72y of one non-bonded portion 72 in the front-back direction LD is preferably within the above range, particularly preferably 30 to 100 mm. In a case where a plurality of the non-bonded portions 72 is disposed, the sum of the sizes 72y of the non-bonded portions 72 in the front-back direction LD is preferably 45 to 100 mm.

Meanwhile, as in the illustrated example, an embodiment is preferable in which an elongated side cover elastic member 75 is disposed in the front-back direction LD at least outside a portion located above the side pocket 70 in the width direction WD in the side cover portion 71, and a portion having the side cover elastic member 75 in the side cover portion 71 is contracted in the front-back direction LD by a contraction force of the side cover elastic member 75. The side cover elastic member 75 may be omitted. However, when the side cover elastic member 75 is disposed, as illustrated in FIGS. 9 and 10, an upper portion of the side cover portion 71 is lifted relative to a lower portion, the side pocket 70 is secured largely, and an opening of the side pocket 70 is easily opened toward the top sheet 30. A rubber thread or the like can be used as the side cover elastic member 75. When a spandex rubber thread is used, the spandex rubber thread preferably has a thickness of 470 to 1240 dtex, and more preferably has a thickness of 620 to 940 dtex. The side cover elastic member 75 preferably has a stretch rate of 150 to 350%, and more preferably has a stretch rate of 200 to 300%.

As in the illustrated example, an embodiment is also preferable in which the opening elastic member 76 is disposed in the front-back direction LD at a position overlapping with at least the non-bonded portion 72 on a back surface side of the non-bonded portion 72 in a thickness direction, and at least a portion overlapping with the non-bonded portion 72 in a thickness direction in the top sheet 30 is contracted in the front-back direction LD by a contraction force of the opening elastic member 76. In the illustrated example, the opening elastic member 76 is disposed between the sheets in a portion on a back surface side of the absorber 56 in the side cover portion 71, but the opening elastic member 76 may be disposed on a front surface side of the absorber 56, for example, between the top sheet 30 and the absorber 56. With such an opening elastic member 76, the top sheet 30 side in the non-bonded portion 72 contracts in the front-back direction LD and becomes shorter, and the size of the side cover portion 71 in the front-back direction LD is excessive. Therefore, the gap 74 between the side cover portion 71 and the top sheet 30 in the non-bonded portion 72 is easily opened.

The side cover portion 71 may be formed of a single sheet material, but a part or the whole thereof may have a stacked structure of a plurality of sheet materials. In particular, as in the illustrated example, an embodiment is preferable in which a cover liquid impervious sheet 77 different from the liquid impervious sheet 11 covering a back surface side of the absorber 56 is continuous along the side cover portion 71 from a portion overlapping with a side of the liquid impervious sheet 11 covering the back surface side of the absorber 56 to at least the side cover elastic member 75 (preferably to the bonded portion 73). By a blocking action of the cover liquid impervious sheet 77, an excretion liquid in the side pocket 70 does not permeate the side cover portion 71, and a waterproof property of the side cover portion 71 can be secured securely. In this case, by covering the entire outer surface of the cover liquid impervious sheet 77 with a side cover sheet 78 formed of a nonwoven fabric, an outer surface of the side cover portion 71 can have a texture like cloth. As the nonwoven fabric used for the side cover sheet 78, a product obtained by subjecting a soft nonwoven fabric having excellent uniformity and concealability, such as a spunbonded nonwoven fabric (SS, SSS, or the like), an SMS nonwoven fabric (SMS, SSMMS, or the like), or a melt blown nonwoven fabric to a water repellent treatment with silicon or the like as necessary can be used suitably. The nonwoven fabric preferably has a fiber basis weight of about 10 to 30 g/m$^2$.

Figure 11:
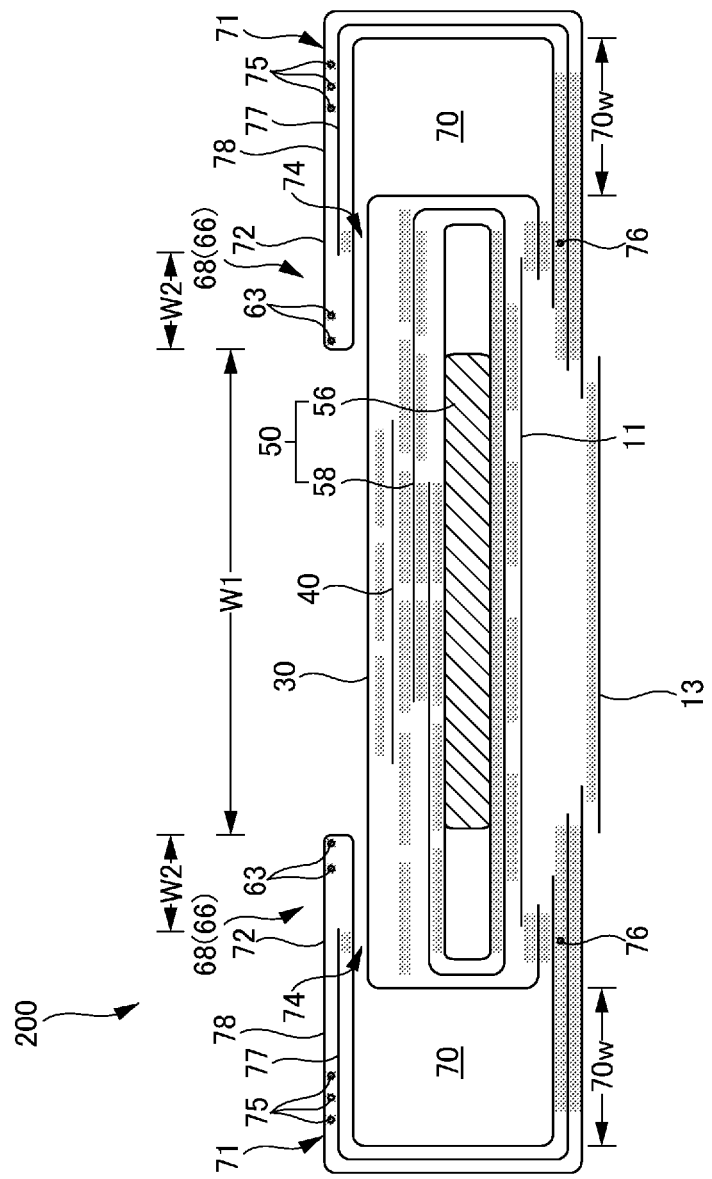
FIG. 11 is a 2-2 cross-sectional view of FIG. 1, illustrating another embodiment.
Figure 12:
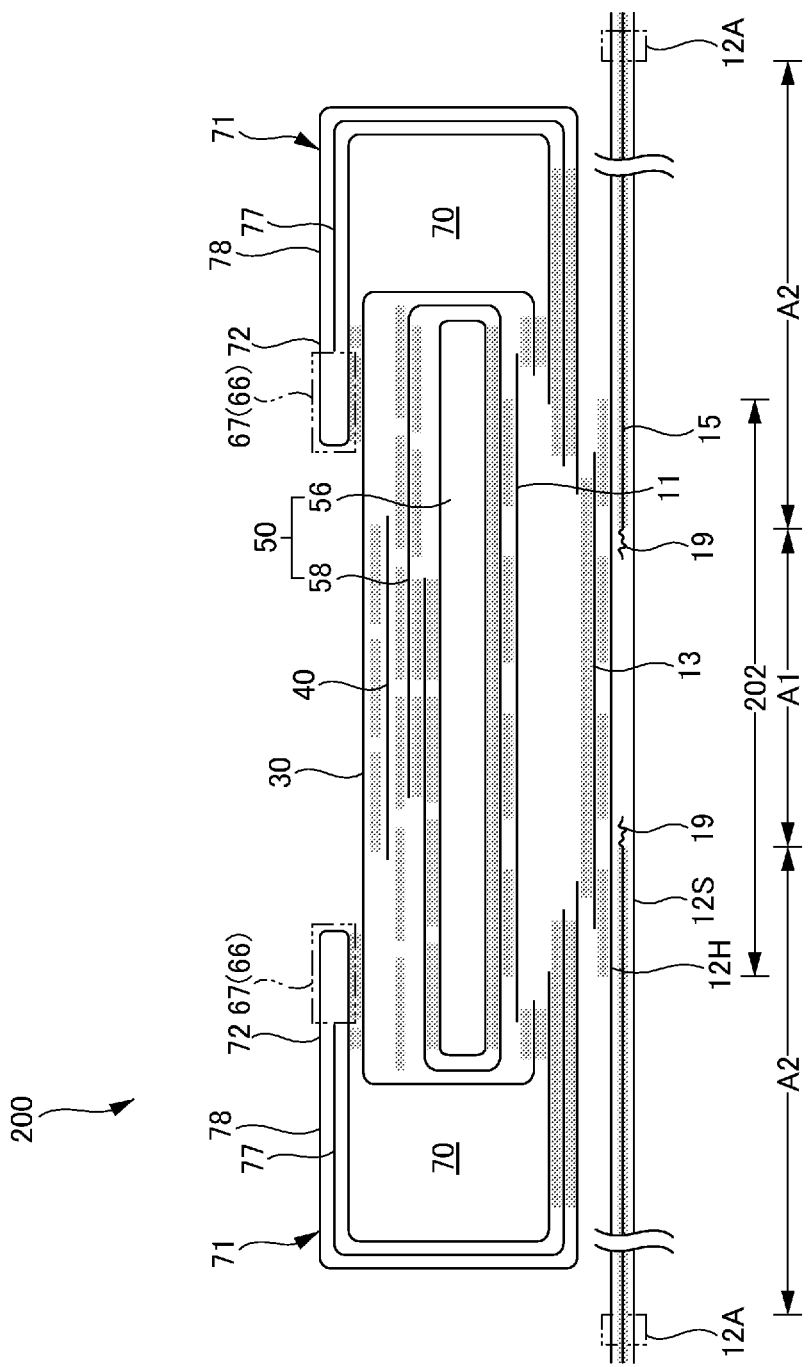
FIG. 12 is a 3-3 cross-sectional view of FIG. 1, illustrating another embodiment.

As illustrated in FIGS. 11 and 12, the cover liquid impervious sheet 77 can be sandwiched between the side cover sheets 78 formed of a nonwoven fabric folded in two to cover the entire cover liquid impervious sheet 77.

Figure 13:
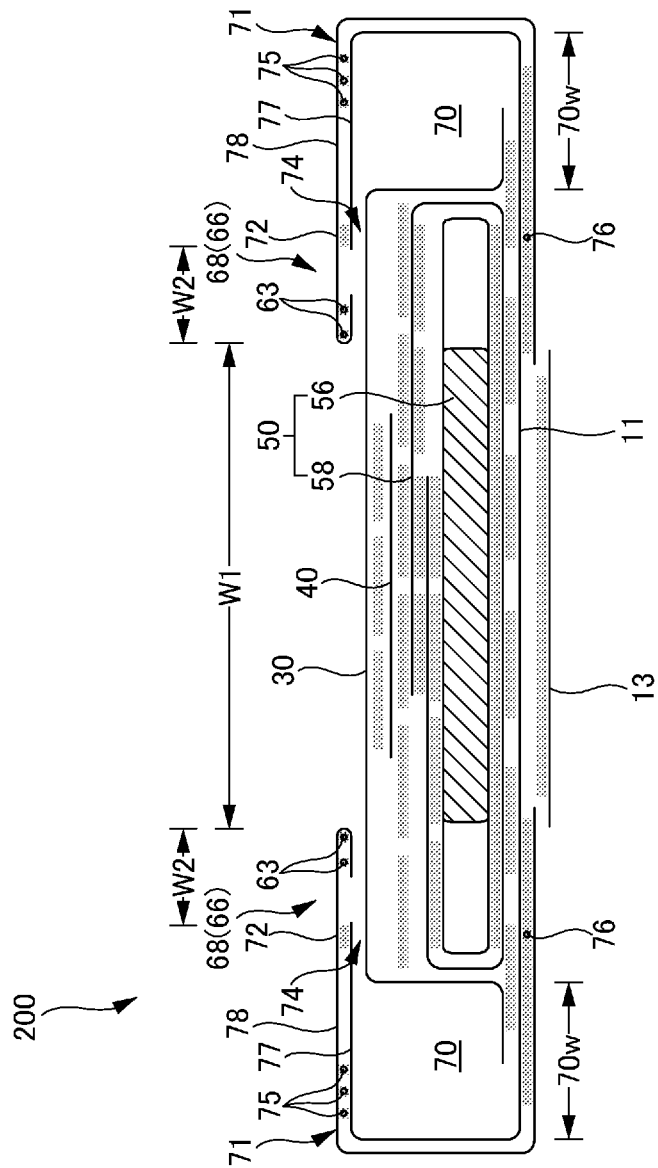
FIG. 13 is a 2-2 cross-sectional view of FIG. 1, illustrating another embodiment.
Figure 14:
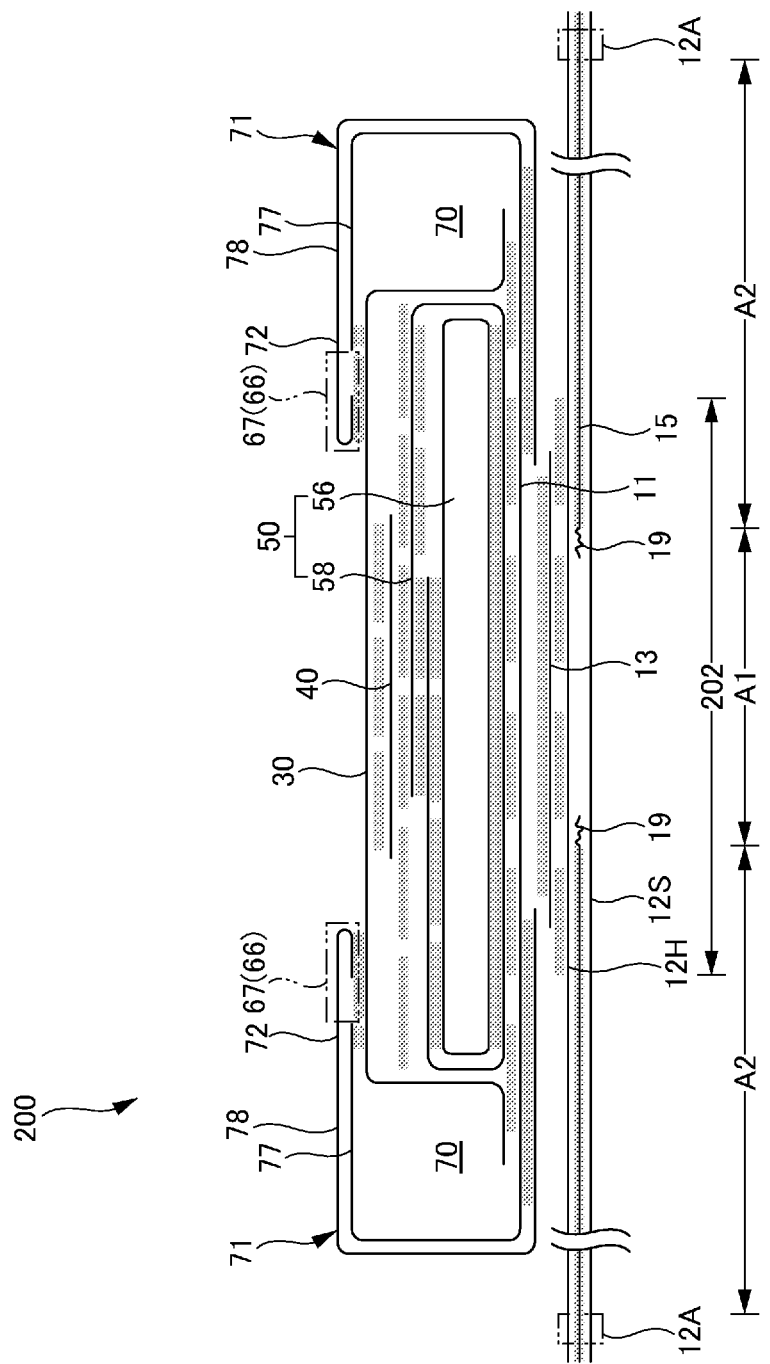
FIG. 14 is a 3-3 cross-sectional view of FIG. 1, illustrating another embodiment.

Without disposing the cover liquid impervious sheet 77 separately from the liquid impervious sheet 11 covering the back surface side of the absorber 56, as illustrated in FIGS. 13 and 14, the liquid impervious sheet 11 covering the back surface side of the absorber 56 may be continuous along the side cover portion 71 from the back surface side of the absorber 56 to at least the side cover elastic member 75 (preferably to the bonded portion 73).

(Rising Gather)

The rising gather 60 is disposed in order to prevent so-called side leakage, and is generally called a three-dimensional gather. As illustrated in FIGS. 9 and 10, the rising gather 60 extends along both sides of the top sheet 30 in the entire front-back direction LD, and rises from the both sides of the top sheet 30 so as to come into contact with a wearer's body surface. In the illustrated example, the rising gather 60 as a whole rises to a center side in the width direction WD. However, an appropriate modification can be made, for example, a root side portion may rise obliquely toward the center side in the width direction WD, and a tip side portion of the intermediate portion may rise obliquely toward the outside in the width direction WD.

In the illustrated example, the side cover portion 71 is formed of the side cover sheet 78 having a portion continuous from a back surface side of the absorber 56 to a side of the top sheet 30 via a lower portion, an outer side, and an upper portion of the side pocket 70, and the side cover sheet 78 has a protruding portion 66 protruding from the non-bonded portion 72 and the bonded portion 73, and the protruding portion 66 forms the rising gather 60. In this way, by forming a portion from the side cover portion 71 to the rising gather 60 with a continuous sheet material, a simpler structure can be obtained. In addition, the gap 74 between the side cover portion 71 and the top sheet 30 in the non-bonded portion 72 is easily opened by a rising action of the rising gather 60.

The illustrated example will be described in more detail. In the rising gather 60, the protruding portion 66 of the side cover sheet 78 constituting the side cover portion 71 is folded back in the width direction WD at a portion to be a tip and folded in two. The protruding portion 66 is a fallen portion 67 fixed to a side surface of the top sheet 30 in a state where both end portions in the front-back direction LD are in a fallen state. An intermediate portion in the front-back direction LD located between the fallen portions 67 is a non-fixed free portion 68. An elongated gather elastic member 63 in the front-back direction LD is fixed in a stretched state between the sheets at least at a tip portion of the free portion 68. For joining opposing surfaces in the fallen portion 67, at least one of a hot melt adhesive by various application methods and a means by material welding such as heat sealing or ultrasonic sealing can be used.

In the rising gather 60 configured as described above, a contraction force of the gather elastic member 63 acts so as to bring the both end portions in the front-back direction closer. However, the both end portions of the protruding portion 66 in the front-back direction are fixed so as not to rise, whereas a portion therebetween is the non-fixed free portion 68. Therefore, only the free portion 68 rises so as to come into contact with a body side as illustrated in FIGS. 9 and 10.

In the illustrated example, the cover liquid impervious sheet 77 of the side cover portion 71 or the liquid impervious sheet 11 located on a back surface side of the absorber 56 does not extend to the protruding portion 66 of the rising gather 60, but can also extend to a part of the protruding portion 66, for example, to a base side.

The number of the gather elastic members 63 disposed in the free portion 68 of the rising gather 60 is preferably 2 to 6, and more preferably 3 to 5. A disposition interval 60*d* between the gather elastic members 63 is suitably 3 to 10 mm. With this configuration, the rising gather 60 easily comes into surface-contact with a skin within a range where the gather elastic member 63. As the gather elastic member 63, a rubber thread or the like can be used. When a spandex rubber thread is used, the spandex rubber thread preferably has a thickness of 470 to 1240 dtex, and more preferably has a thickness of 620 to 940 dtex. The gather elastic member 63 preferably has a stretch rate of 150 to 350%, and more preferably has a stretch rate of 200 to 300%.

The size of the rising gather 60 can be appropriately determined. However, in a case of baby applications, for example, as illustrated in FIG. 3, a rising height W2 of the rising gather 60 (a length of the protruding portion 66 in the width direction WD in an unfolded state) is preferably 15 to 60 mm, and particularly preferably 20 to 40 mm. A separation distance W1 between innermost portions in a flatly folded state is preferably 60 to 190 mm, and particularly preferably 70 to 140 mm such that the rising gather 60 is parallel to a surface of the top sheet 30. In a case of adult applications, the rising height W2 of the rising gather 60 (a length of the protruding portion 66 in the width direction WD in an unfolded state) is preferably 20 to 60 mm, and particularly preferably 30 to 55 mm. The separation distance W1 between innermost portions in a flatly folded state is preferably 110 to 190 mm, and particularly preferably 120 to 150 mm such that the rising gather 60 is parallel to a surface of the top sheet 30.

The structure of the rising gather 60 is not particularly limited, and may be formed by attaching a member other than the side cover portion 71.

Meanwhile, for bonding layers in the side cover portion 71 and the rising gather 60 and fixing the side cover elastic member 75 and the gather elastic member 63 sandwiched between the layers, at least one of a hot melt adhesive by various application methods and a fixing means by material welding such as heat sealing or ultrasonic sealing can be used. However, when the entire portions between the layers are bonded, flexibility is impaired. Therefore, preferably, a portion other than bonded portions of the side cover elastic member 75 and the gather elastic member 63 is not bonded or weakly bonded. In the illustrated embodiment, by applying a hot melt adhesive only to outer peripheral surfaces of the side cover elastic member 75 and the gather elastic member 63 by an application means such as a comb gun or a SureWrap nozzle, and sandwiching the side cover elastic member 75 and the gather elastic member 63 between layers of the side cover portion 71 and the rising gather 60, the side cover elastic member 75 and the gather elastic member 63 are fixed, and the layers are fixed only with the hot melt adhesive applied to the outer peripheral surfaces of the side cover elastic member 75 and the gather elastic member 63.

Similarly, with regard to fixing of the cover liquid impervious sheet 77 and the side cover sheet 78 incorporated in the side cover portion 71, at least one of a hot melt adhesive by various application methods and a fixing means by material welding such as heat sealing or ultrasonic sealing can be used.

Explanation of Terms in Specification

The following terms in the specification have the following meanings unless otherwise specified in the specification.

"Front-back direction (longitudinal direction)" means a direction connecting a ventral side (front side) and a dorsal side (back side), and "width direction" means a direction (horizontal direction) orthogonal to the front-back direction.

"Front surface side" means a side closer to a wearer's skin when an underpants-type disposable diaper is worn. "Back surface side" means a side far from a wearer's skin when an underpants-type disposable diaper is worn.

"Stretch rate" means a value obtained when a natural length is 100%.

"Gel strength" is measured as follows. To 49.0 g of artificial urine (mixture of 2% by weight of urea, 0.8% by weight of sodium chloride, 0.03% by weight of calcium chloride dihydrate, 0.08% by weight of magnesium sulfate heptahydrate, and 97.09% by weight of deionized water), 1.0 g of a super absorbent polymer is added, and the resulting mixture is stirred with a stirrer. The gel thus generated is left in a thermohygrostat at 40° C.×60% RH for three hours. Thereafter, the temperature is returned to room temperature, and gel strength is measured with a curdmeter (Curdmeter-MAX ME-500 manufactured by I. Techno Engineering Co., Ltd.).

"Basis weight" is measured as follows. A sample or a test piece is predried and then left in a test chamber or an apparatus in a standard state (test location is at a temperature of 20±5° C. and a relative humidity of 65% or less) so as to have a constant weight. Predrying refers to causing a sample or a test piece to have a constant weight in an environment that a relative humidity is 10 to 25% and a temperature does not exceed 50° C. Incidentally, fibers having an official moisture regain of 0.0% do not have to be predried. A sample of 200 mm×250 mm (±2 mm) in size is cut out from a test piece having a constant weight using a template for sampling (200 mm×250 mm (±2 mm)). The weight of the sample is measured. The weight is multiplied by 20 to calculate the weight per square meter to be used as a basis weight.

"Thickness" is automatically measured under conditions that a load is 0.098 N/cm$^2$ and a pressing area is 2 cm$^2$ using an automatic thickness meter (KES-G5 handy compression measuring program).

Water absorption capacity is measured in accordance with JIS K7223-1996 "Test method for water absorption capacity of super absorbent polymer".

Water absorption rate is "time to end point" when JIS K7224-1996 "Test method for water absorption rate of super absorbent polymer" is performed using 2 g of super absorbent polymer and 50 g of physiological saline.

"Unfolded state" means a flatly unfolded state without contraction or slackness.

The size of each portion means a size not in a natural length state but in an unfolded state unless otherwise specified.

In a case where environmental conditions in a test and a measurement are not described, the test and the measurement are performed in a test room or an apparatus in a standard state (test location is at a temperature of 20±5° C. and a relative humidity of 65% or less).

INDUSTRIAL APPLICABILITY

The present invention is suitable for an underpants-type disposable diaper as in the above example, but can be applied to a general absorbent article such as a sanitary napkin as well as a tape-type or a pad-type disposable diaper.

REFERENCE SIGNS LIST

11 Liquid impervious sheet
12B Back outer body
12F Front outer body
12H Inner sheet layer
12S Outer sheet layer
13 Cover nonwoven fabric
17 Waist portion elastic member
19 Unnecessary elastic member
200 Inner body
201, 202 Inner and outer bonded portion
30 Top sheet
40 Intermediate sheet
50 Absorbent element
56 Absorber
58 Wrapping sheet
60 Rising gather
63 Gather elastic member
66 Protruding portion
67 Falling portion
68 Free portion
70 Side pocket
71 Side cover portion
72 Non-bonded portion
73 Joined portion
74 Gap
75 Side cover elastic member
76 Opening elastic member
77 Cover liquid impervious sheet
78 Side cover sheet
A1 Non-stretchable region
A2 Stretchable region
L Intermediate region
LD Front-back direction
T Lower torso
U Under-waist portion
W Waist portion
WD Width direction
WO Waist opening

The invention claimed is:

1. An absorbent article comprising:
an absorber;
a top sheet covering a front surface side of the absorber;
a liquid impervious sheet covering a back surface side of the absorber; and
rising gathers rising from both sides of the top sheet,
wherein a side pocket extending in a front-back direction is disposed on a lateral side of the absorber,
wherein the side pocket is surrounded by a side cover portion formed of a sheet material reaching a back surface side of the absorber continuously from above a side of the top sheet via an upper portion, an outer side, and a lower portion of the side pocket,
wherein a portion of the side cover portion located above the side of the top sheet includes a non-bonded portion not bonded to the top sheet and a bonded portion located on both front and back sides of the non-bonded portion,
wherein a gap between the side cover portion and the top sheet in the non-bonded portion is open above the top sheet and toward the side pocket,
wherein the sheet material further includes a protruding portion protruding from the non-bonded portion and the bonded portion, and the protruding portion forms the rising gather,
wherein an elongated side cover elastic member is disposed in the front-back direction at least outside a portion located above the side pocket in a width direction in the side cover portion, and
wherein a portion having the side cover elastic member in the side cover portion is contracted in the front-back direction by a contraction force of the elongated side cover elastic member.

2. The absorbent article according to claim 1, wherein a liquid impervious sheet covering a back surface side of the absorber is continuous along the side cover portion from a back surface side of the absorber to at least the side cover elastic member, or a cover liquid impervious sheet different from the liquid impervious sheet covering the back surface side of the absorber is continuous along the side cover portion from a portion overlapping with the liquid impervious sheet covering the back surface side of the absorber to at least the side cover elastic member.

3. The absorbent article according to claim 1, wherein an opening elastic member is disposed in a front-back direction at a position overlapping with at least the non-bonded portion on a back surface side of the non-bonded portion in a thickness direction; and
at least a portion overlapping with the non-bonded portion in a thickness direction in the top sheet is contracted in the front-back direction by a contraction force of the opening elastic member.

4. The absorbent article according to claim 1, wherein the non-bonded portion has a size of 15 to 100 mm in a front-back direction.

5. The absorbent article according to claim 1, wherein a plurality of the non-bonded portions are disposed at intervals in a front-back direction in an intermediate portion in the front-back direction.

6. The absorbent article according to claim 1, wherein an inner space of the side pocket has a size of 5 mm or more in a width direction.

* * * * *